US009289607B2

(12) United States Patent
Su et al.

(10) Patent No.: US 9,289,607 B2
(45) Date of Patent: Mar. 22, 2016

(54) URGENCY THERAPY WITH NEUROMODULATION AND C-AFFERENT NERVE DESENSITIZATION

(75) Inventors: Xin Su, Plymouth, MN (US); Gregory F. Molnar, Fridley, MN (US); Dwight E. Nelson, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 357 days.

(21) Appl. No.: 13/817,486

(22) PCT Filed: Aug. 16, 2011

(86) PCT No.: PCT/US2011/047903
§ 371 (c)(1),
(2), (4) Date: Jul. 30, 2013

(87) PCT Pub. No.: WO2012/024286
PCT Pub. Date: Feb. 23, 2012

(65) Prior Publication Data
US 2014/0142549 A1 May 22, 2014

Related U.S. Application Data

(60) Provisional application No. 61/374,921, filed on Aug. 18, 2010.

(51) Int. Cl.
*A61N 1/02* (2006.01)
*A61N 1/36* (2006.01)
(Continued)

(52) U.S. Cl.
CPC .......... *A61N 1/36007* (2013.01); *A61K 31/165* (2013.01); *A61M 5/14276* (2013.01);
(Continued)

(58) Field of Classification Search
CPC ............ A61N 1/36007; A61N 1/0521; A61N 1/36107; A61N 1/36057; A61M 5/14276; A61M 5/1723
USPC ............................................... 607/41, 40, 143
See application file for complete search history.

(56) References Cited

U.S. PATENT DOCUMENTS 5,330,515 A 7/1994 Rutecki et al.
6,802,841 B2 10/2004 Utley et al.
(Continued)

OTHER PUBLICATIONS

Chancellor, M.B., "New Frontiers in the Treatment of Overactive Bladder and Incontinence," *Rev Urol*, 2002;4 Suppl 4:S50-6.
(Continued)

*Primary Examiner* — Theodore Stigell
*Assistant Examiner* — Michael Carey
(74) *Attorney, Agent, or Firm* — Shumaker & Sieffert, P.A.

(57) ABSTRACT

Systems (10), devices (16), and methods may be used for treating bladder dysfunction, such as urgency and pelvic pain. In one example, a method includes administering a pharmacological agent to a patient (14) in a dosage sufficient to desensitize a C-afferent nerve fiber of the patient. Additionally, the method includes delivering stimulation to activate a nerve fiber proximate to the C-afferent nerve fiber via an electrode (19A, 19B, 21A, 21B, 29A-29D) electrically coupled to an implantable medical device (16). In some examples, the nerve fiber may be different than the C-afferent nerve fiber, the stimulation of the nerve fiber may elicit an inhibitory physiological response related to voiding in the patient, and/or the stimulation substantially may not activate the C-afferent nerve fiber after desensitization of the nerve fiber via the administration of the pharmacological agent.

34 Claims, 10 Drawing Sheets

(51) Int. Cl.
  *A61M 5/142* (2006.01)
  *A61M 5/172* (2006.01)
  *G06F 19/00* (2011.01)
  *A61K 31/165* (2006.01)

(52) U.S. Cl.
  CPC .......... *A61M5/1723* (2013.01); *A61N 1/3606* (2013.01); *A61N 1/36057* (2013.01); *A61N 1/36171* (2013.01); *G06F 19/3481* (2013.01); *A61M 2205/054* (2013.01); *A61M 2210/1085* (2013.01); *A61N 1/36071* (2013.01); *G06F 19/3468* (2013.01)

(56) References Cited

U.S. PATENT DOCUMENTS

| | | | |
|---|---|---|---|
| 6,879,859 | B1 | 4/2005 | Boveja |
| 7,276,057 | B2 | 10/2007 | Gerber |
| 7,328,069 | B2 | 2/2008 | Gerber |
| 7,427,280 | B2 | 9/2008 | Gerber |
| 7,429,387 | B2 | 9/2008 | Schmidt |
| 2005/0033374 | A1* | 2/2005 | Gerber ............................ 607/39 |
| 2007/0255333 | A1* | 11/2007 | Giftakis ............. A61N 1/36007 607/39 |
| 2010/0121314 | A1 | 5/2010 | Iobbi |

OTHER PUBLICATIONS

Cruz, F., et al., "Resiniferatoxin and Botulinum Toxin Type A for Treatment of Lower Urinary Tract Symptoms," *Neurourol Urodyn* Oct. 2007;26(6 Suppl):920-7.

De Groat, W.C., et al., "Afferent Nerve Regulation of Bladder Function in Health and Disease," *Handb Exp Pharmacol*, 2009; (194):91-138.

Fowler, C.J., "Bladder Afferents and Their Role in the Overactive Bladder," *Urology*, May 2002; 59(5 Suppl 1): 37-42.

George, J., et al., "The Effectiveness of Intravesical Oxybutynin, propantheline, and Capsaicin in the Management of Neuropathic Bladder Following Spinal Cord Injury," *ScientificWorldJournal*, Oct. 22, 2007;7:1683-90.

Hussain, I.F., et al., "Use of Intravesical Capsaicin for Urge Urinary Incontinence and Irritative Voiding Syndromes," *Curr Opin Urol*. Jul. 1998;8(4):293-6.

MacDonald, R., et al., "Neurotoxin Treatments for Urinary Incontinence in Subjects with Spinal Cord Injury or Multiple Sclerosis: A Systematic Review of Effectiveness and Adverse Effects," *J Spinal Cord Med*. 2008;31(2):157-65.

* cited by examiner

URGENCY THERAPY WITH NEUROMODULATION AND C-AFFERENT NERVE DESENSITIZATION

This application claims the benefit of U.S. Provisional Application No. 61/374,921, entitled "URGENCY THERAPY WITH NEUROMODULATION AND C-AFFERENT NERVE DESENSITIZATION," and filed on Aug. 18, 2010.

TECHNICAL FIELD

The disclosure relates to therapy for bladder dysfunction and/or pelvic pain.

BACKGROUND

Bladder dysfunction, such as urgency (overactive bladder) or urinary incontinence, is a problem that may afflict people of all ages, genders, and races. Various muscles, nerves, organs and conduits within the pelvic floor cooperate to collect, store and release urine. A variety of disorders may compromise urinary tract performance, and contribute to urgency or urinary incontinence. Many of the disorders may be associated with aging, injury, or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. Nerves running though the pelvic floor stimulate contractility in the sphincter. An improper communication between the nervous system and the urethra or urinary sphincter can result in a bladder dysfunction, such as urgency (overactive bladder), urge incontinence, or another type of urinary incontinence.

SUMMARY

In general, the disclosure is directed to devices, systems, and techniques for managing bladder dysfunction, such as urgency (overactive bladder) or urinary incontinence. In some examples, the devices, systems, and techniques described herein alternatively or additionally may be utilized to manage fecal urgency, fecal incontinence or pelvic pain. In some examples, bladder dysfunction may be managed by administering a pharmacological agent to a patient. The pharmacological agent may be administered to cause desensitization of C-afferent nerve fiber(s). In this manner, the C-afferent nerve fibers may be desensitized to neuromodulation, e.g., electrical stimulation, that is delivered to manage bladder dysfunction. In some examples, the pharmacological agent may be administered to cause desensitization, e.g., desensitization to neuromodulation or electrical stimulation, of C-afferent nerve fiber(s) that innervate the bladder or urethra. As used herein, desensitization can include a reduction in response of the C-afferent nerve fiber(s) to external stimuli, such as electrical stimulation. In some examples, the nerve that includes the desensitized C-afferent nerve fiber(s) may include a spinal nerve, a sacral nerve, a pelvic nerve, a pudendal nerve, a dorsal genital nerve, a tibial nerve, an inferior rectal nerve, a perineal nerve, or branches of any of the aforementioned nerves.

In addition to the delivery of the administration of the pharmacological agent, bladder dysfunction may be managed by delivering stimulation therapy to at least one nerve via electrodes electrically connected to an implantable medical device (IMD), e.g., via a lead or on an outer housing of the IMD. In some examples, the at least one nerve to which the IMD delivers stimulation therapy may comprise the nerve that includes the C-afferent nerve fiber(s) to which the pharmacological agent has been administered. In other examples, neuromodulation may be delivered to a different nerve than the nerve that includes the desensitized C-afferent nerve fibers. In some examples, the nerve to which the IMD delivers stimulation may include a spinal nerve, a sacral nerve, a pelvic nerve, a pudendal nerve, a dorsal genital nerve, a tibial nerve, an inferior rectal nerve, a perineal nerve, or branches of any of the aforementioned nerves.

In some examples, the IMD may receive an indication that the pharmacological agent has been administered to the patient, e.g., via a patient programmer or from a drug delivery device. In some implementations, the IMD may select a stimulation therapy program based on the indication and may deliver electrical stimulation therapy in accordance with the selected stimulation therapy program.

In some examples, the desensitization of the C-afferent fibers may increase a therapeutic efficacy of the electrical stimulation therapy. For example, the stimulation therapy may more effectively decrease a rate of bladder contractions when used in combination with desensitization of the C-afferent fibers. Alternatively or additionally, desensitization of the C-afferent fibers may allow an increase in stimulation intensity above a stimulation intensity that would cause patient discomfort when the C-afferent fibers are not desensitized.

In one aspect, the disclosure is directed to an implantable medical device including a therapy delivery module configured to generate and deliver stimulation therapy to a patient via an electrode electrically coupled to the therapy delivery module, and a control module. According to this aspect of the disclosure, the control module is configured to receive an indication that a pharmacological agent has been administered to the patient, select a stimulation therapy program based on the indication, and control the therapy delivery module to generate and deliver electrical stimulation therapy in accordance with the stimulation therapy program. The pharmacological agent desensitizes a C-afferent nerve fiber in the patient, and the stimulation therapy may elicit an inhibitory physiological response related to voiding in the patient.

In another aspect, the disclosure is directed to a system including an implantable drug delivery device configured to administer a pharmacological agent to a patient in a dosage sufficient to desensitize a C-afferent nerve fiber of the patient. According to this aspect of the disclosure, the system further includes an implantable medical device configured to deliver electrical stimulation therapy according to a stimulation therapy program to a nerve fiber proximate to the C-afferent nerve fiber via an electrode electrically coupled to the implantable medical device. The nerve fiber may be different than the C-afferent nerve fiber, and the stimulation of the nerve fiber may elicit an inhibitory physiological related to voiding. In some examples, the stimulation substantially does not activate the C-afferent nerve fiber.

In a further aspect, the disclosure is directed to a method that includes administering a pharmacological agent to a patient in a dosage sufficient to desensitize a C-afferent nerve fiber of the patient. Additionally, the method includes delivering electrical stimulation to activate a nerve fiber proximate to the C-afferent nerve fiber via an electrode electrically coupled to an implantable medical device. In accordance with this aspect of the disclosure, the nerve fiber may be different than the C-afferent nerve fiber, the stimulation of the nerve fiber may elicit an inhibitory physiological related to voiding in the patient, and the stimulation substantially may not activate the C-afferent nerve fiber.

In an additional aspect, the disclosure is directed to a method that includes receiving via a control module of an implantable medical device an indication that a pharmacological agent has been administered in a dosage sufficient to desensitize a C-afferent nerve fiber to a patient in which the implantable medical device is implanted. Additionally, the method includes selecting via the control module a stimulation therapy program based on the received indication, and controlling via the control module a therapy delivery module to generate and deliver electrical stimulation therapy in accordance with the stimulation therapy program. In some examples, the stimulation therapy elicits an inhibitory physiological response related to voiding in the patient.

In a further aspect, the disclosure is directed to a computer-readable medium comprising instructions that cause a processor to receive via an implantable medical device an indication that a pharmacological agent has been administered in a dosage sufficient to desensitize a C-afferent nerve fiber to a patient in which the implantable medical device is implanted. According to this aspect of the disclosure, the instructions further cause the processor to select a stimulation therapy program based on the received indication, and control a therapy delivery module to generate and deliver electrical stimulation therapy in accordance with the stimulation therapy program. In some examples, the stimulation therapy elicits an inhibitory physiological response related to voiding in the patient.

In another aspect, the disclosure is directed to a system including means for administering a pharmacological agent to a patient in a dose sufficient to desensitize a C-afferent nerve fiber and means for delivering electrical stimulation to activate a nerve fiber proximate to the C-afferent nerve fiber via an electrode electrically coupled to the means for delivering stimulation. According to this aspect of the disclosure, the nerve fiber may be different than the C-afferent nerve fiber, the stimulation of the nerve fiber may elicit an inhibitory physiological related to voiding in the patient, and the stimulation substantially may not activate the C-afferent nerve fiber.

In an additional aspect, the disclosure is directed to a system including means for receiving an indication that a pharmacological agent has been administered to a patient in a dosage sufficient to desensitize a C-afferent nerve fiber in the patient, means for selecting a stimulation therapy program based on the received indication, and means for generating and delivering electrical stimulation therapy in accordance with the stimulation therapy program. According to this aspect of the disclosure, the stimulation therapy may elicit an inhibitory physiological response related to voiding in the patient.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more examples are set forth in the accompanying drawings and the description below.

DETAILED DESCRIPTION

Described herein are devices, systems, and techniques for managing bladder dysfunction, such as, for example, urgency, overactive bladder, and/or incontinence. In some examples, bladder dysfunction of a patient is managed by at least administering a pharmacological agent to a patient, where the pharmacological agent desensitizes a C-afferent nerve fiber of the patient, and delivering stimulation to a nerve fiber proximate to the C-afferent nerve fiber via an electrode that is electrically coupled to an implantable medical device. In some examples, the stimulation of the nerve fiber may elicit an inhibitory physiological response by the patient that is related to voiding, such as a reduction in a bladder contraction frequency in the patient. Because the C-afferent nerve fiber is desensitized by the delivery of the pharmacological agent, the stimulation of the nerve fiber proximate to the C-afferent nerve fiber may not activate the desensitized C-afferent nerve fiber or may not activate the desensitized C-afferent nerve fiber as strongly (compared to prior to desensitization of the C-afferent nerve fiber) in some examples. In some examples, the C-afferent nerve fiber may be a relatively small nerve fiber of the same peripheral nerve that is captured by the electrical stimulation, e.g., neuromodulation or neurostimulation, delivered to the patient. In other examples, the C-afferent nerve fiber may be a relatively small nerve fiber of a different peripheral nerve than the peripheral nerve that is captured by the electrical stimulation delivered to the patient.

Desensitization of a C-afferent nerve fiber in combination with electrical stimulation therapy may provide synergistic therapeutic effects that may help manage bladder dysfunction. For example, because a relatively high intensity electrical current stimulation configured to reduce bladder contractions may inadvertently activate C-afferent nerve fibers, thereby possibly reducing the efficacy of the stimulation, desensitization of the C-afferent nerve fiber may potentiate the inhibitory action of the high intensity current stimulation.

Figure 1:
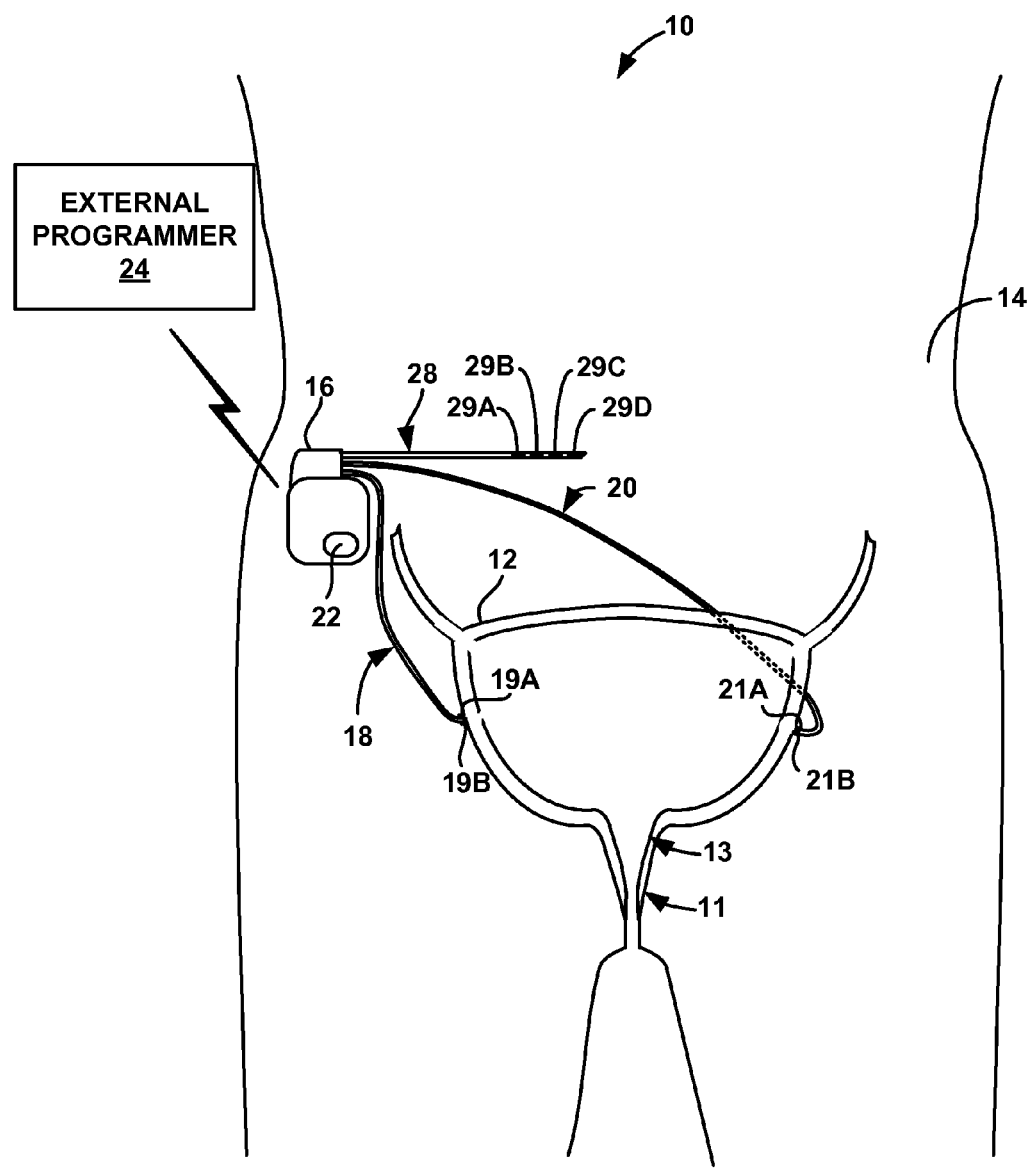
FIG. 1 is a conceptual diagram that illustrates an example therapy system that delivers electrical stimulation therapy to a patient to generate an inhibitory physiological response by the patient related to voiding.

FIG. 1 is a conceptual diagram that illustrates an example therapy system 10 that delivers electrical stimulation therapy to patient 14 to generate an inhibitory physiological response by patient 14 related to voiding to manage a dysfunction of bladder 12 of patient 14. For example, the inhibitory physiological response may include a reduction in contraction frequency of bladder 12. Therapy system 10 includes an implantable medical device (IMD) 16, which is coupled to leads 18, 20, and 28 and sensor 22. System 10 also includes an external programmer 24, which communicates with IMD 16 via a wireless communication protocol. In accordance with aspects of this disclosure, system 10 may deliver electrical stimulation therapy via IMD 16 to patient 14 after a pharmacological agent that desensitizes a C-afferent nerve fiber has been administered to patient 14. In some examples, IMD 16 may deliver electrical stimulation therapy to a nerve fiber proximate to the C-afferent nerve fiber to which the pharmacological agent has been administered. In some aspects, the pharmacological agent may be delivered before delivery of electrical stimulation, during delivery of electrical stimulation, or both.

IMD 16 generally operates as a therapy device that delivers electrical stimulation to, for example, a target tissue site proximate a spinal nerve, a sacral nerve, a pelvic nerve, a pudendal nerve, dorsal genital nerve, a tibial nerve, an inferior rectal nerve, a perineal nerve, or branches of any of the aforementioned nerves. IMD 16 provides electrical stimulation therapy to patient 14 by generating and delivering a programmable electrical stimulation signal (e.g., in the form of electrical pulses or an electrical waveform) to a target therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, and 21B) and stimulation electrodes, such as electrodes 29, to a sensing module and a therapy delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases.

One or more medical leads, e.g., leads 18, 20, and 28, may be electrically and mechanically connected to IMD 16 and surgically or percutaneously tunneled to place one or more electrodes carried by a distal end of the respective lead at a desired nerve, muscle or other tissue site, e.g., one of the previously listed target therapy sites such as a tissue site proximate a spinal, sacral, pudendal, dorsal genital, tibial, inferior rectal, or a perineal nerve. For example, lead 28 may be positioned such that electrodes 29 deliver a stimulation therapy to a capture (e.g., stimulate to modulate activity of) a spinal, sacral, pudendal, dorsal genital, tibial, inferior rectal, or a perineal nerve to reduce a frequency of contractions of bladder 12. Electrodes 29 of the common lead 28 may deliver stimulation to the same or different nerves. In FIG. 1, leads 18 and 20 are placed proximate to an exterior surface of the wall of bladder 12 at first and second locations, respectively. Electrodes 19 and 21 carried by leads 18 and 20, respectively, may or may not be used to deliver stimulation therapy to a target tissue site proximate bladder 12 (e.g., a nerve that innervates bladder 12). In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects for first and second stimulation therapies (e.g., reducing a contraction frequency of bladder 12 and promoting closure of a urinary sphincter). In some examples, one or more of leads 18, 20, 28 may be, at least in part, paddle-shaped (e.g., a "paddle" lead), and may include an array of electrodes on a common surface, which may or may not be substantially flat (e.g., planar).

In some examples, one or more of electrodes 19, 21, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize or reduce discomfort to patient 14 that results from the delivery of electrical stimulation therapy. An electrical field may define the volume of tissue that is affected when the electrodes 19, 21, 29 are activated (e.g., electrodes may be activated when IMD 16 delivers a stimulation signal with the electrodes). An activation field represents the neurons that will be activated by the electrical field in the neural tissue proximate to the activated electrodes.

In some examples, one or more of electrodes 19, 21, 29 may be physically configured or implanted in a manner that allows selective stimulation of afferent nerve fibers or selective stimulation of efferent nerve fibers. For example, as described above, one or more of electrodes 19, 21, 29 may comprise a segmented electrode that may allow generation of electrical fields that target a specific fiber or group of fibers in a nerve or a branch of a nerve. Stimulation delivery by a segmented electrode may be directed in a direction less than substantially around the entire outer perimeter of a cylindrical lead. Alternatively, or additionally, the implantation location and orientation of one or more of electrodes 19, 21, 29 may allow generation of electrical fields that target a specific fiber or group of fibers in a nerve or a branch of a nerve. Similarly, one or more of electrodes 19, 21, 29 may be implanted proximate to a nerve or a branch of a nerve that includes substantially only afferent nerve fibers or substantially only efferent nerve fibers.

In one example, one or more of electrodes 19, 21, 29 are implanted proximate to, and target for stimulation therapy, a nerve that includes at least one of Aβ (A-beta) afferent nerve fibers, Aδ (A-delta) afferent nerve fibers, and C-afferent nerve fibers. Aβ (A-beta) afferent nerve fibers and Aδ (A-delta) afferent nerve fibers may have larger diameters than C-afferent nerve fibers and are myelinated. C-afferent nerve fibers may be sensory nerve fibers that are unmyelinated and have a smaller average diameter relative to Aβ (A-beta) afferent nerve fibers and Aδ (A-delta) afferent nerve fibers. Electrical stimulation of Aβ (A-beta) afferent nerve fibers and/or Aδ (A-delta) afferent nerve fibers may play a role in reducing a contraction frequency of bladder 12.

In other examples, one or more of electrodes 19, 21, 29 may target a nerve or a branch of a nerve that includes only efferent nerve fibers or both afferent and efferent nerve fibers.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies to respective stimulation sites within patient 14 or for monitoring at least one physiological parameter of patient 14.

IMD 16 may deliver stimulation therapy substantially continuously or periodically over an extended period of time, e.g., chronic stimulation, to at least one of a spinal nerve, a sacral nerve, a pelvic nerve, a pudendal nerve, dorsal genital nerve, a tibial nerve, an inferior rectal nerve, a perineal nerve to generate an inhibitory physiological response by patient 14 related to voiding by patient 14. In some examples, the inhibitory physiological response includes a reduction in contraction frequency of bladder 12. Reduction of a contraction frequency of bladder 12 may reduce the patient's feeling of needing to void or empty bladder 12, e.g., may reduce symptoms of urgency.

As described above, therapy system 10 may be utilized in conjunction with administration of a pharmacological agent to patient 14. The pharmacological agent may affect a sensitivity of at least one C-afferent nerve fiber. In some examples, the at least one C-afferent nerve fiber may be in a nerve to which IMD 16 delivers stimulation. In other examples, the at least one C-afferent nerve fiber may form part of a different nerve than the nerve to which IMD 16 delivers stimulation. Spinal nerves, such as a sacral nerve, and branches of spinal nerves may include different classes of nerve fibers, including, for example, Aβ (A-beta) afferent nerve fibers, Aδ (A-delta) afferent nerve fibers, and C-afferent nerve fibers. Nerve fibers may have stimulation thresholds (e.g., stimulation intensities at which the nerve fiber is activated) that are approximately proportionate to their diameters. For example, Aβ (A-beta) afferent nerve fibers and Aδ (A-delta) afferent nerve fibers may begin being activated at relatively low stimulation intensities, while C-afferent fibers may be activated at higher stimulation intensities. As described elsewhere in this disclosure, an electrical stimulation intensity may be a function of, for example, any one or more of a current amplitude of the stimulation signal, a voltage amplitude of the stimulation signal, a frequency or pulse rate of the stimulation signal, the shape of the stimulation signal, a duty cycle of the stimulation signal, a pulse width of the stimulation signal, or the combination of electrodes 29 and respective polarities of the subset of electrodes 29 used to deliver the stimulation signal.

In nerves that innervate bladder 12, some C-afferent fibers respond to low intensity distention of bladder 12 and are active during rhythmic contraction of bladder 12. It is believed that C-afferent fiber activation may promote contraction of bladder 12. Thus, if IMD 16 delivers stimulation therapy to a nerve that innervates bladder 12 and activates C-afferent nerve fibers, the stimulation therapy may promote contraction of bladder 12 (e.g., thereby increasing sensations of urge perceived by patient 14), contrary to the desired effect of the stimulation therapy (e.g., reduction of contraction frequency of bladder 12). Alternatively or additionally, stimulation therapy that activates C-afferent nerve fibers may cause patient 14 to experience discomfort or pain in connection with the stimulation therapy. Desensitization of C-afferent nerve fibers prior to delivering, or during delivery of, electrical stimulation therapy via IMD 16 may result in more efficacious stimulation therapy, may allow greater freedom in selecting stimulation parameters (e.g., parameters that define a higher stimulation intensity) without patient discomfort or pain to patient 14, or both. For example, desensitization of C-afferent nerve fibers may decrease the extent to which the stimulation may activate of the C-afferent nerve fibers in a manner that competes with the objectives of the stimulation therapy, e.g., to reduce bladder contractions and/or the urge perceived by patient 14.

A pharmacological agent may desensitize at least one C-afferent nerve fiber of patient 14, i.e., may reduce a sensitivity and/or response of the at least one C-afferent nerve fiber to stimuli, such as electrical stimulation therapy provided by IMD 16. In some examples, the pharmacological agent may render the at least one C-afferent nerve fiber substantially insensitive to stimuli, such as electrical stimulation therapy. The pharmacological agent may desensitize the C-afferent nerve fiber by, for example, modifying electrophysiological excitability of the C-afferent nerve fiber or modifying an activation potential of the C-afferent nerve fiber. For example, the pharmacological agent may lower an activation potential of the C-afferent nerve fiber. Lowering the activation potential of the C-afferent nerve fiber may increase the electrical stimulation intensity that is sufficient to activate the C-afferent nerve fiber (e.g., increase the stimulation threshold), thus increasing a stimulation intensity that may be delivered by IMD 16 without activating the C-afferent nerve fiber.

Examples of pharmacological agents that may affect a sensitivity of C-afferent nerve fibers include, but are not limited to, vanilloid receptor (VR1) (which may also be known as the transient receptor potential cation channel subfamily V member 1 (TRPV1)) agonists in sufficiently high doses, VR1 (TRPV1) antagonists, capsaicin in sufficiently high doses, sodium (Na+) channel blockers, calcium (Ca++) channel blockers, botulinum toxin (e.g., Botox®), or the like. As used herein, "sufficiently high doses" refers to doses in sufficient quantities of active ingredient that C-afferent fibers are not activated to cause pain or discomfort in patient 14, but instead are desensitized. Hence, desensitization may be to a degree sufficient to prevent or at least partially reduce activation of the C-afferent nerve fiber during delivery of electrical stimulation therapy. For example, at relatively low doses, capsaicin may activate C-afferent fibers and may cause pain or discomfort. In sufficiently high doses, capsaicin may desensitize C-afferent fibers. In some examples, whether a dose is sufficiently high or not may be influenced by, for example, the manner and location of administration of the dose, and/or the manner and location of delivery of electrical stimulation. In some examples, capsaicin may be administered locally to bladder 12 by intravesical injection.

In some examples, desensitizing the C-afferent nerve fiber of a target nerve, or a nerve other than the nerve to which IMD 16 delivers stimulation, prior to delivering stimulation therapy to the target nerve (e.g., a tissue site proximate the target nerve) via IMD 16 may provide benefits to the stimulation therapy, e.g., because the activation of the C-afferent nerve fiber during electrical stimulation therapy may interfere with the desired effects of the stimulation therapy or may reduce an efficacy of the stimulation therapy. For example, activation of the C-afferent nerve fiber during stimulation therapy may reduce the intended inhibitory physiological effect of the stimulation therapy (e.g., may result in the stimulation therapy producing an inhibitory physiological effect that is less inhibitory than is intended). As described above, this may be due to activation of C-afferent nerve fibers promoting rhythmic contraction of bladder 12. By desensitizing the C-afferent nerve fiber, stimulation of the nerve that innervates bladder 12 of the patient may be more efficacious, e.g., may further reduce a frequency of bladder contractions at a particular stimulation intensity, compared to if the C-afferent nerve fiber is not desensitized by the administration of a pharmacological agent in accordance with techniques described herein.

In other examples, desensitization of the at least one C-afferent nerve fiber may allow a greater range of stimulation parameter values according to which IMD 16 delivers efficacious stimulation therapy to patient 14 compared to the range of stimulation parameter values that may be used when the C-afferent nerve fiber is not desensitized. For example, desensitization of the at least one C-afferent nerve fiber may allow IMD 16 to deliver stimulation therapy at a higher stimulation intensity, which may provide efficacious therapy to patient 14, than could be delivered when the at least one C-afferent nerve fiber is not desensitized. While not wishing to be bound by theory, desensitization of the at least one C-afferent nerve fiber may reduce or substantially eliminate discomfort or pain experienced by patient 14 due to stimulation therapy delivered via IMD 16 to at least the same nerve fiber, thus allowing IMD 16 to deliver higher intensity stimulation therapy to patient 14 with reduced patient discomfort. Hence, in some examples, desensitization may refer to reducing sensitivity of a nerve to electrical stimulation therapy, via delivery of the pharmacological agent, to prevent or reduce activation of C-afferent nerve fibers in the presence of electrical stimulation.

The pharmacological agent may be administered via one or more of a variety of administration methods, such as, for example, oral introduction, intravesical (in bladder 12) introduction, intradetrusor introduction, intrathecal introduction, epidural introduction, via an implantable drug delivery device (see FIG. 3), or the like.

In some examples, the pharmacological agent may be administered to patient 14 prior to a time period during which IMD 16 delivers stimulation to the nerve fiber, during the time period when IMD 16 delivers stimulation to the nerve fiber, and/or after the time period when IMD 16 delivers stimulation to the nerve fiber. For example, the pharmacological agent may be administered to patient 14 prior to a time period during which IMD 16 delivers stimulation to the nerve fiber when the pharmacological agent induces relatively long-term desensitization of the C-afferent nerve fiber, e.g., the pharmacological agent may induce desensitization of the C-afferent nerve fiber that remains after administration of the pharmacological agent for a time period on the order of hours (e.g., less than a day), days (e.g., less than a week), weeks (e.g., less than a year), years (e.g., less than a decade), decades, or substantially indefinitely (e.g., indefinitely or nearly indefinitely). In some examples, additionally or alternatively, the pharmacological agent may be administered during delivery of electrical stimulation therapy. In some examples, the desensitization of the C-afferent nerve fiber may be permanent, e.g., the C-afferent nerve fiber may be desensitized for the remainder of the life of patient 14. In other examples, the desensitization of the C-afferent nerve fiber may return to a normal (i.e., pre-treatment) sensitivity over the course of time after administration of the pharmacological agent, e.g., after termination of administration of the pharmacological agent.

Regardless of the therapeutically efficacious duration for the pharmacological agent, the pharmacological agent may be administered any length of time prior to delivery of stimulation therapy to patient 14 by IMD 16. In some examples, the pharmacological agent may be administered to patient 14 sufficiently prior to delivery of stimulation therapy by IMD 16 so that the pharmacological agent has time to act on the C-afferent nerve fiber and desensitize the C-afferent nerve fiber prior to delivery of stimulation. Additionally or alternatively, the pharmacological agent may be administered to patient 14 sufficiently close in time to, or during, delivery of stimulation therapy by IMD 16 so that the C-afferent nerve fiber is desensitized for at least a portion of the time during which IMD 16 delivers stimulation therapy to patient 14.

In some examples, the pharmacological agent may be administered to patient 14 in a single dose or a dose cycle including a plurality of doses prior to beginning delivery of stimulation therapy to patient 14 by IMD 16. For example, the pharmacological agent may be administered to patient 14 in a single dose that includes all the pharmacological agent used to desensitize the C-afferent nerve fiber for the desired period of time. As another example, the pharmacological agent may be administered to patient 14 in a series of doses that each includes a portion of the pharmacological agent used to desensitize the C-afferent nerve fiber, the entire series of doses making up the dose cycle. In some examples, a single dose or single dose cycle of pharmacological agent may be utilized to desensitize the C-afferent nerve fiber when the pharmacological agent desensitizes the C-afferent nerve fiber for a sufficiently long time, e.g., a year(s), decade(s), indefinitely, or substantially permanently.

In other examples, the pharmacological agent may be administered to patient 14 periodically. In some examples, the period may be determined, at least in part, by the duration for which the pharmacological agent desensitizes the C-afferent nerve fiber. For example, a pharmacological agent may desensitize the C-afferent nerve fiber for a period of about one year. In such an example, the pharmacological agent may be administered to patient 14 in approximately one-year intervals (e.g., intervals of slightly less than one year, such as 11 months or 11.5 months) so the C-afferent nerve fibers are substantially continuously desensitized. In other examples, the pharmacological agent may desensitize the C-afferent nerve fiber for longer or shorter periods of time, and the frequency of administration of the pharmacological agent may accordingly be higher or lower. For example, the pharmacological agent may be administered to patient 14 periodically, and the period may be measured in seconds, minutes, hours, days, months, years, decades, or the like.

In some examples, the pharmacological agent may be administered at regular intervals, e.g., periodically, irregular intervals, or substantially continuously, e.g., via an external or drug delivery device. The drug delivery device may administer the pharmacological agent at a predetermined rate (e.g., microliters per hour; μL/h), dosage, and bolus size. In some examples, the administration of the pharmacological agent may truly be continuous, e.g., via a peristaltic pump, while in other examples, the administration of the pharmacological agent may be discontinuous or periodic, but the periods or discontinuities may be sufficiently small that the delivery may be considered substantially continuous. For example, the pharmacological agent may be delivered periodically with a period that is measured in seconds or fractions of a second, or the pharmacological agent may be delivered by a piston pump or other pump that delivers pulses of the pharmacological agent. Further details regarding administering a pharmacological agent via a drug delivery device will be presented below with respect to FIGS. 3 and 5. Additionally, in some examples, the pharmacological agent may be administered periodically via a drug delivery device, e.g., with a period that is measured in hours, days, months, or the like.

In some examples, the drug delivery device may administer (or deliver) the pharmacological agent according to at least one pharmacological therapy program. The pharmacological therapy program may define parameters according to which the drug delivery device delivers the pharmacological agent. For example, the pharmacological therapy program may specify a schedule of different pharmacological agent delivery rates and/or other parameters by which the drug delivery device delivers the pharmacological agent to patient 14.

In some examples, a pharmacological therapy program stored on the drug delivery device defines one or more pharmacological agent doses to be delivered from the drug delivery device to patient 14. A dose of pharmacological agent generally refers to a total amount of pharmacological agent, e.g., measured in milligrams or other volumetric units, delivered over a total amount of time, e.g., per day or twenty-four hour period. The amount of pharmacological agent in a dose may convey to a caregiver an indication of the probable efficacy of the agent and the possibility of side effects.

A sufficient amount of the pharmacological agent is administered to patient 14 in order to have a desired therapeutic effect, such as desensitization of at least one C-afferent nerve fiber. This dosage may be determined by a clinician for a specific patient 14 or the dosage may be selected to be applicable to a plurality of patients. The amount of the pharmacological agent delivered to patient 14 may be limited to a maximum amount, such as a maximum daily amount, in order to limit or avoid potential side effects. Pharmacological therapy program parameters specified by a user, e.g., via a programmer, may include fluid volume per dose, dose time period, and/or maximum dose for a given time interval, e.g., daily. In some examples, dosage may also prescribe particular concentrations of active ingredients in the pharmacological agent delivered by the drug delivery device to patient 14.

The manner in which a dose of pharmacological agent is automatically delivered to patient 14 by the drug delivery device may also be defined in the therapy program. For example, a control module of the drug delivery device may be programmed to deliver a dose of pharmacological agent according to a schedule that defines different rates at which the agent is to be delivered at different times during the dose period, e.g. a twenty-four hour period. The pharmacological agent rate refers to the amount, e.g. in volume, of pharmacological agent delivered over a unit period of time, which may change over the course of the dose period as the drug delivery device delivers the dose of agent to patient 14.

In some examples, the pharmacological therapy program may include other parameters, including, e.g., time intervals between successive pharmacological agent doses.

In some examples, the pharmacological agent may be administered to patient 14 so that C-afferent nerve fibers are desensitized in the nerve targeted during stimulation therapy delivery by IMD 16, while in other examples, the pharmacological agent may be administered so that C-afferent nerve fibers are desensitized in a nerve other than the nerve targeted during stimulation therapy delivered by IMD 16. For example, the pharmacological agent may be administered to patient 14 so that C-afferent nerve fibers are desensitized in a nerve or nerves located in or near the target therapy site (e.g., proximate to electrodes 29), such that delivery of stimulation to the target therapy site may inadvertently activate and/or stimulate the C-afferent nerve fibers in the nerve or nerves located near the target tissue site. In other examples, the pharmacological agent may be administered to patient 14 so that C-afferent nerve fibers are desensitized at a location along the nerve or nerves other than within the target therapy site. For example, the pharmacological agent may be administered to patient 14 to desensitize C-afferent nerve fibers in a location either upstream or downstream of the target therapy site (e.g., in a direction in which electrical signals travel from in the nerve or in a direction in which electrical signals travel to in the nerve). The C-afferent nerve fibers may be selected such that that delivery of stimulation to the target therapy site by IMD 16 may inadvertently activate and/or stimulate the C-afferent nerve fibers. In other examples, the pharmacological agent may be administered intravesically (within bladder 12) via a drug delivery device or via transcutaneous injection provided by patient 14, a clinician or another patient caregiver. Additionally or alternatively, the pharmacological agent may be administered to patient 14 via for example, oral introduction, intradetrusor introduction, intrathecal introduction, epidural introduction, or the like.

Returning now to delivery of stimulation therapy by IMD 16, in some examples, after the C-afferent fiber(s) has been desensitized, IMD 16 may deliver stimulation therapy via at least one of electrodes 29 according to a stimulation therapy program. The stimulation therapy program may define various parameters of the stimulation signal and electrode configuration which result in a predetermined stimulation intensity being delivered to the targeted nerve. In some examples, the therapy program defines values for at least one of a current amplitude of the stimulation signal, a voltage amplitude of the stimulation signal, a frequency or pulse rate of the stimulation signal, the shape of the stimulation signal, a duty cycle of the stimulation signal, a pulse width of the stimulation signal, or the combination of electrodes 29 and respective polarities of the subset of electrodes 29 used to deliver the stimulation signal. Together, these stimulation parameter values define the stimulation intensity (also referred to herein as a stimulation intensity level).

In some examples, the therapy program according to which IMD 16 delivers therapy may define a first time period and a second time period. IMD 16 may deliver stimulation at a first stimulation intensity during the first time period(s) and may deliver stimulation at a second stimulation intensity that is less than the first stimulation intensity during the second time period(s) that immediately follow respective first time period (s). As described above, the second stimulation intensity may include substantially no stimulation intensity, i.e., in some examples, delivering stimulation at the second stimulation intensity may include ceasing delivery of stimulation during the second time period. For sake of conciseness, the description herein will be directed primarily to ceasing delivery of stimulation during the second time period. However, in other examples, the various examples of techniques described herein may include delivery of stimulation via IMD 16 at a first, higher intensity during the first time period and delivery of stimulation via IMD 16 at a second, reduced stimulation intensity during the second time period.

The therapy program may define a stimulation intensity which elicits a first inhibitory physiological response related to voiding of patient 14 during the first time period, while IMD 16 delivers the stimulation therapy. In some examples, the stimulation therapy elicits substantially no inhibitory physiological response related to voiding of patient 14 during the first time period. In other words, the physiological response of patient 14 during the first time period may be substantially unchanged from the physiological response of patient 14 prior to IMD 16 delivering any stimulation therapy 16. In some examples, the physiological response comprises a contraction frequency of bladder 12. Accordingly, in some cases, a contraction frequency of bladder 12 is substantially the same prior to stimulation therapy and during the first time period. In other examples, the contraction frequency of bladder 12 is reduced during the first time period compared to the contraction frequency of bladder 12 prior to IMD 16 delivering stimulation to patient 14.

The stimulation therapy delivered by IMD 16 may elicit a second inhibitory physiological response of patient 14 during a second time period immediately following the first time period, during which the IMD 16 does not deliver stimulation therapy to patient 14. The second inhibitory physiological response may also be related to voiding and, in some examples, for at least a portion of the second time period, may be greater than the first inhibitory physiological response. For example, the contraction frequency of bladder 12 may be lower for at least a portion of the second time period compared to the bladder contraction frequency during the first time period. In this way, the stimulation therapy delivered by IMD 16 during the first time period may produce a post-stimulation inhibitory effect that extends beyond the first time period.

In some examples, the first and second time periods may have durations on the order of minutes (e.g., less than one hour). For example, the first time period, during which IMD 16 delivers stimulation therapy, may be between about 5 minutes and about 20 minutes. Similarly, the second time period, during which IMD 16 ceases to deliver stimulation therapy, may be between about 5 minutes and about 30 minutes. In some examples, the relative lengths of the first and second time periods may be selected to provide advantageous battery life to IMD 16 compared to an IMD 16 that delivers stimulation therapy substantially continuously.

Additionally or alternatively, it is believed that a stimulation pattern that includes first and second time periods, each on the order of minutes, may reduce neuron habituation or other forms of patient adaptation to the stimulation therapy and extend an effective lifetime of the stimulation therapy (e.g., the time for which the stimulation therapy is efficacious in reducing bladder contraction frequency). It has been found that patient 14 may adapt to stimulation delivered by IMD 16 over time, such that a certain level of electrical stimulation provided to a tissue site in patient 14 may be less effective over time. This phenomenon may be referred to as "adaptation." As a result, any beneficial effects to patient 14 from the electrical stimulation may decrease over time. While the electrical stimulation levels (e.g., amplitude of the electrical stimulation signal) may be increased to overcome such adaptation, the increase in stimulation levels may consume more power, and may eventually reach undesirable levels of stimulation.

In some examples, the therapy program with which IMD 16 generates and delivers therapy to patient 14 may define a stimulation intensity which is less than, equal to, or greater than a threshold stimulation intensity (also referred to as a threshold intensity), which can be a physiological intensity threshold or a therapeutic intensity threshold. In some examples, the physiological intensity threshold level may be defined as the stimulation intensity at which an acute, physiologically significant response of a patient is first observed when increasing the stimulation intensity from a low intensity to a higher intensity. Stated another way, the physiological intensity threshold may be defined as approximately the lowest stimulation intensity that elicits an acute, physiologically significant response of the patient. In some examples, the physiological response may be different than the therapeutic response (e.g., an inhibitory physiological response) elicited by the delivery of electrical stimulation at the first stimulation intensity (or the second stimulation intensity, which is described below). The acute, physiologically significant response may or may not be perceived by the patient. In some examples, an acute response may be defined as a physiological response that occurs within about 30 seconds or less (e.g., about 10 seconds) of the patient receiving the stimulation (e.g., the initiation of the stimulation at the particular intensity level).

The acute physiological response that is used to determine the physiological intensity threshold may be manifest in a number of different examples. For example, the acute physiological response may be a motor response, a stimulation perception response, or a detected physiological response, such as a nerve action potential. A stimulation perception response may be observed and reported by the patient, e.g., as a paresthesia or other sensation. However, a motor response or a physiological response (e.g., a nerve impulse or non-therapeutic effect) may be reported by the patient, observed by a clinician, or automatically detected by one or more sensors internal or external to the patient. In some examples, whether a response is physiologically significant may be defined by the patient. For example, the stimulation may elicit movement of a toe of the patient, and the patient may define the movement of the toe as physiologically significant when the movement of the toe is perceptible or when the movement of the toe is above some arbitrary amount defined by the patient or the clinician.

In other examples, the threshold intensity level may be a therapeutic intensity threshold (also referred to as a therapeutic threshold) in that the stimulation is insufficient to cause a desired therapeutic effect during delivery of stimulation (e.g., during the first time period). However, the stimulation is sufficient to cause the desired therapeutic effect after the stimulation is terminated (e.g., during the second time period). In some examples, this means that the electrical stimulation does not cause any significant therapeutic effect, or any therapeutic effects, during delivery stimulation (e.g., during the first time period). In other examples, however, the electrical stimulation may cause some detectable therapeutic effect during delivery of stimulation (e.g., during the first time period), but the therapeutic effect may be of a lesser magnitude than the desired therapeutic effect produced after termination of stimulation (e.g., during the second time period). As one example, if the desired therapeutic effect is a desired level of reduction in bladder contraction frequency, the stimulation may be insufficient to produce the desired therapeutic effect during delivery of stimulation (e.g., during the first time period) if it causes no therapeutic effect in reducing bladder contraction frequency or if it causes a level of therapeutic effect that is less than the desired level of reduction of bladder contraction frequency.

The threshold intensity may be determined experimentally for each patient. An iterative stimulation procedure may be used to determine the threshold intensity. The iterative procedure may be performed by a clinician, for example, using IMD 16 implanted in patient 14, or another device, or automatically by IMD 16. In one example, a clinician may begin the determination of the threshold intensity level with a stimulation intensity that is not likely to produce any acute physiologically significant response, in the case of a physiological intensity threshold, or a therapeutic response from the patient, in the case of a therapeutic intensity threshold. This intensity may be selected, for example, based on the clinician's knowledge in some cases. The clinician can select the initial intensity by, for example, setting stimulation parameters (e.g., a current amplitude, a voltage amplitude, a frequency or pulse rate, a shape, a pulse width, a duty cycle, and/or the combination of electrodes) to produce a relatively low stimulation intensity and controlling IMD 16 to deliver stimulation to patient 14 using these parameters. Then, the clinician may incrementally increase one or more stimulation parameters, e.g., a current amplitude, pulse width, or pulse frequency, until an acute physiological response or therapeutic response to the stimulation is detected. Once the desired response is detected, the stimulation parameter may define the threshold intensity.

For example, in the case of a physiological intensity threshold, if no physiological response is observed in response to the stimulation at the initial intensity level, a value of one stimulation parameter may be changed to increase the stimulation intensity while the remaining parameters are kept approximately constant, and IMD 16 may be controlled to deliver stimulation at the new stimulation intensity. The stimulation parameter that is selected may be known to affect stimulation intensity. The process of modifying the stimulation parameter value and delivering stimulation according at the respective stimulation intensity level may be repeated until a threshold physiological response is observed (e.g., based on a signal generated by an implanted or external sensor or patient input indicating a perception of a physiological event). In this way, the process of finding the threshold intensity level may be an iterative procedure. The desired response can be detected, for example, based on a signal generated by sensor 22 or patient input indicating a perception of a physiological event. Other physiological responses may be detected when stimulating other nerves of patient 14.

The threshold physiological response (also referred to herein as a "threshold response") may include a perception of the stimulation by the patient, or an observed response of a muscle that is driven by the nerve being stimulated at the target site, for example, a sphincter contraction, a toe twitch, or a detected signal on an electromyography (EMG). Other physiological responses may be detected when stimulating other nerves of patient 14. In some examples, perception of the stimulation by patient 14 may occur prior to an observed response of a muscle that is being driven by the nerve being stimulated. In other words, the perception of the stimulation by patient 14 may occur at a lower threshold than the motor threshold. When stimulating one of the nerves described herein, such as a spinal nerve, sacral nerve, pudendal nerve, or the like, the physiological response may be a contraction of a toe of patient 14, a flexing of an anal sphincter of patient 14, or a detected signal on an EMG. Other physiological responses may be detected when stimulating other nerves of patient 14.

In one example, the threshold intensity level may be determined by setting the stimulation frequency at about 10 Hz to about 14 Hz and increasing the current amplitude until a muscle response is observed based on a sensor input (e.g., EMG indicating the muscle movement) or patient input (e.g., perception of the stimulation by the patient).

In some examples, based on the determined threshold stimulation intensity, the clinician may select the stimulation parameters for therapy delivery to patient 14. For example, the stimulation parameter values may be changed such that the therapy program defines a stimulation intensity that is between about 50% (half) and about 300% (three times) the threshold intensity. While in some examples, delivering stimulation therapy at an intensity that is three times a threshold intensity may result in discomfort or pain in patient 14, desensitizing C-afferent nerve fibers prior to delivering stimulation therapy to patient 14 may reduce or substantially eliminate discomfort or pain for patient 14, allowing use of higher stimulation intensities than otherwise may be used. Increasing the stimulation intensity may, for example, increase the efficacy of stimulation therapy in reducing bladder contractions or otherwise minimizing or eliminating bladder urge symptoms of patient 14. Thus, the techniques described herein that desensitize C-afferent fibers may help provide more efficacious stimulation therapy to patient 14.

The stimulation intensity may be changed by adjusting at least one of the stimulation parameters described above, such as, for example, a current amplitude of the stimulation signal, a voltage amplitude of the stimulation signal, a frequency of the stimulation signal, a pulse rate of the stimulation signal, a pulse width of the stimulation signal, the shape of the stimulation signal, the duty cycle of the stimulation signal, or the combination of electrodes 29. For example, the current and/or voltage amplitude of the stimulation signal may be reduced to reduce an intensity of the stimulation signal or increased to increase an intensity of the stimulation signal. IMD 16 may generate and deliver the stimulation signal as substantially continuous waveforms or as a series of pulses.

In some implementations, IMD 16 may receive a notification that the pharmacological agent has been administered to patient 14, and may control delivery of stimulation therapy based on the received notification. IMD 16 may receive the indication from a user, such as a clinician, via external programmer 24, or may receive the indication from a drug delivery device (e.g., implantable drug delivery device 42 shown in FIG. 3) if it is separate from IMD 16.

In some examples, IMD 16 may select a stimulation therapy program based on the received indication. For example, IMD 16 may select a stimulation therapy program that includes stimulation parameters that define a higher stimulation intensity than IMD 16 would otherwise select if the pharmacological agent had not been administered to patient 14. As described above, in some examples, desensitization of the C-afferent nerve fibers by the pharmacological agent may facilitate use of a higher stimulation intensity by reducing discomfort or pain experienced by patient 14 due to the stimulation therapy. In other examples, IMD 16 may select a stimulation therapy program that includes stimulation parameters that define a relatively lower stimulation intensity (e.g., within a range of stimulation intensities which IMD 16 would select when the pharmacological agent had not been administered to patient 14). As described above, in some examples, activation of C-afferent fibers that innervate bladder 12 may promote contraction of bladder 12, thus inhibiting an efficacy of the stimulation therapy when the C-afferent fibers are activated. In some examples, desensitization of the C-afferent fibers may therefore increase an efficacy of the stimulation therapy delivered by IMD 16. IMD 16 may then deliver the stimulation therapy to patient 14 in accordance with the selected stimulation therapy program.

In some examples, IMD 16 may deliver the stimulation therapy in an open loop manner, in which IMD 16 delivers stimulation according to the stimulation parameters and does not modify the stimulation parameters in response to a detected physiological parameter or input from patient 14.

In other examples, IMD 16 may deliver the stimulation therapy in a closed loop manner or a pseudo-closed loop manner, e.g., IMD 16 may control at least one stimulation parameter based on feedback received from a user, such as patient 14, or a physiological sensor. For example, IMD 16 may modify at least one parameter of the stimulation therapy when IMD 16 detects a contraction frequency of bladder 12 that exceeds a particular threshold. In some implementations, such as the one shown in FIG. 1, IMD 16 determines an impedance through bladder 12, which varies as a function of the contraction of bladder 12, via electrodes 19 and 21 on leads 18 and 20, respectively. In the example shown in FIG. 1, IMD 16 may determine impedance of bladder 12 using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine impedance of bladder 12 based on the transmitted electrical signal. Such an impedance measurement may be utilized to determine response of contractions of bladder 12 to stimulation therapy, to determine a fullness of bladder 12, or the like.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 19 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In the example of FIG. 1, IMD 16 also includes a sensor 22 for detecting changes in the contraction of bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which therapy system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a signal generated by sensor 22. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples IMD 16 may control at least one parameter of the stimulation therapy the based on input received from sensor 22.

One example of a stimulation parameter that may be controlled in closed loop therapy includes a duration of the second time period(s), in stimulation therapy that include a plurality of interleaved first and second time periods. In some examples, IMD 16 may sense contractions of bladder 12 during a time period prior to delivery of the stimulation therapy to establish a baseline contraction frequency of bladder 12 or the baseline contraction frequency may be stored in a memory of IMD 16 or another device (e.g., programmer 24). IMD 16 may sense contractions of bladder 12 via one or more means, such as, for example, electrodes 19 or 21, or sensor 22. The bladder contraction may be detected via any suitable sensing mechanism. For example, the IMD may detect bladder contraction based on, for example, bladder impedance, bladder pressure, pudendal or sacral afferent nerve signals, a urinary sphincter EMG, or any combination thereof. IMD 16 then may utilize the sensed contractions of bladder 12 to determine a baseline contraction frequency of bladder 12, e.g., as a number of contractions of bladder 12 per unit time. The baseline contraction frequency of bladder 12 may represent the patient state when no therapeutic effects from delivery of stimulation by IMD 16 are present. In some cases, however, patient 14 may also receive other types of therapy for managing bladder dysfunction, such as a pharmaceutical agent, which may be different than the pharmacological agent delivered to desensitize C-afferent fibers of a nerve to which IMD 16 delivers stimulation or C-afferent fibers of a nerve that is different than the nerve to which IMD 16 delivers stimulation. The baseline contraction frequency of bladder 12 may represent the patient state when patient 14 is under the influence of the pharmaceutical agent that is delivered to manage bladder dysfunction.

After determining a baseline contraction frequency, IMD 16 may then sense via electrodes 19 or 21 or sensor 22 a contraction frequency of bladder 12 during the second time period, after the first time period during which IMD 16 delivers stimulation therapy to patient 14. In some examples, IMD 16 may sense a contraction frequency of bladder 12 periodically throughout the second time period, e.g., once per minute within the second time period. IMD 16 may compare the contraction frequency of bladder 12 during the second time period to the baseline contraction frequency or a threshold frequency that is based on the baseline contraction frequency. The threshold frequency may be less than the baseline contraction frequency. In some examples, when the contraction frequency sensed during the second time period is within a certain, predetermined value (e.g., and stored in IMD 16, programmer 24 or another device) of the baseline contraction frequency or is above the threshold frequency, IMD 16 may initiate delivery of the stimulation therapy, e.g., restart the first time period. In some examples, the pharmacological agent may have already been delivered to patient 14 prior to IMD 16 initiating delivery of the stimulation therapy. In other examples, a control module of IMD 16 may generate and transmit an instruction to a control module of a drug delivery device (e.g., implantable drug delivery device 42 shown in FIG. 3) to administer the pharmacological agent when the control module of IMD 16 determines that the contraction frequency of bladder 12 is within a certain value of the baseline contraction frequency or is above the threshold frequency.

System 10 may also include an external programmer 24, as shown in FIG. 1. In some examples, programmer 24 may be a wearable communication device, with activation of the second stimulation therapy integrated into a key fob or a wrist watch, handheld computing device, computer workstation, or networked computing device. Programmer 24 may include a user interface that receives input from a user (e.g., patient 14, a patient caretaker or a clinician). In some examples, the user interface includes, for example, a keypad and a display, which may for example, be a cathode ray tube (CRT) display, a liquid crystal display (LCD), a light emitting diode (LED) display, or an organic light-emitting diode (OLED). The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16. The user may also interact with a programmer to program IMD 16, e.g., select values for the stimulation parameter values with which IMD 16 generates and delivers stimulation and/or the other operational parameters of IMD 16. For example, the user may use a programmer to retrieve information from IMD 16 regarding the contraction of bladder 12 and/or voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected. Additionally, the user may interact with programmer 24 or another separate programmer to communicate an indication to IMD 16 that the pharmacological agent has been administered to patient 14.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
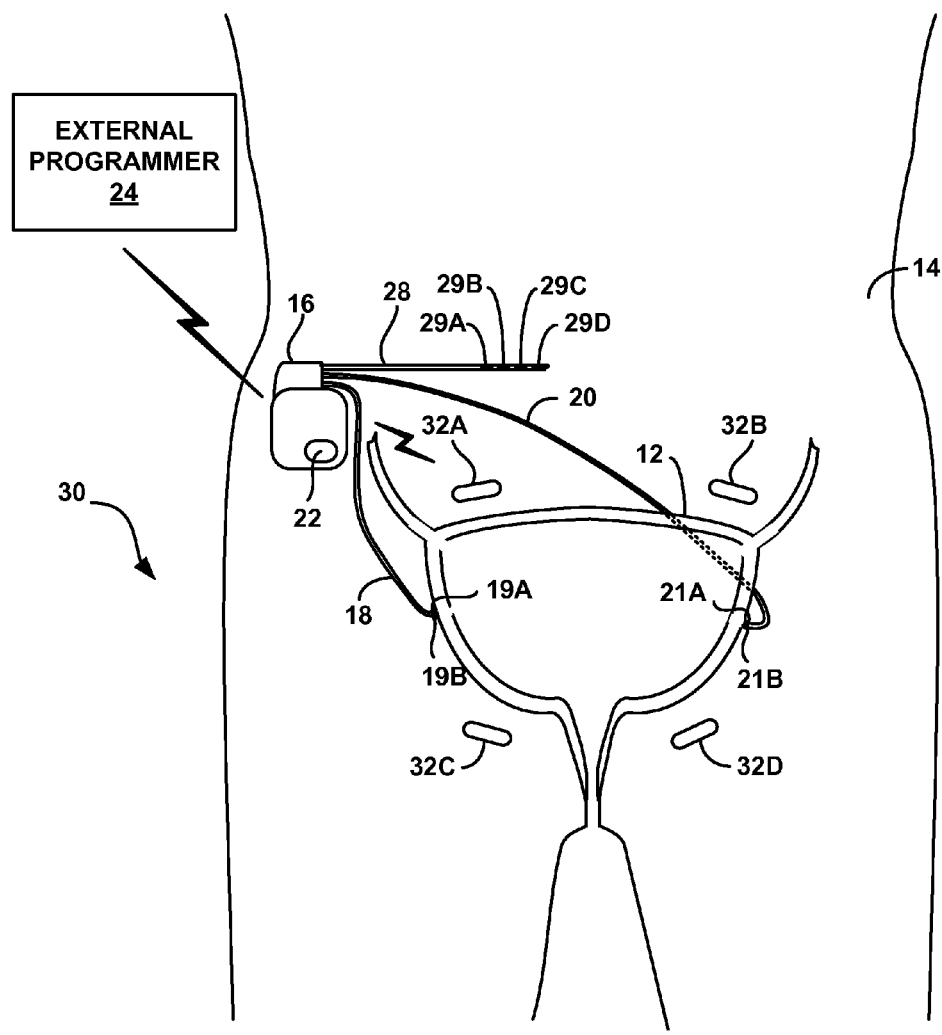
FIG. 2 is a conceptual diagram that illustrates another example therapy system that delivers electrical stimulation therapy to a patient to generate an inhibitory physiological response by the patient related to voiding.

FIG. 2 is conceptual diagram illustrating another example of a therapy system 30 that delivers stimulation therapy to generate an inhibitory physiological response in patient 14 to manage a bladder dysfunction of patient 14. Similar to therapy system 10 described with reference to FIG. 1, therapy system 30 may be utilized in conjunction with administering a pharmacological agent that desensitizes C-afferent fibers prior to, during, or after stimulation therapy delivery via therapy system 30. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 vie one or more electrodes, which may be on an outer housing of microstimulator 32. Microstimulators 32 have a smaller size than IMD 16, and are typically leadless.

IMD 16 may deliver the stimulation therapy to patient 14 via microstimulators 32. For example, IMD 16 may communicate wirelessly with microstimulators 32 via wireless telemetry to control delivery of the stimulation therapy via microstimulators 32. In other examples, microstimulators 32 may control therapy delivery without the aid of IMD 16. For example, one or more of the microstimulators 32 may include a processor that controls the delivery of therapy to elicit a physiological response of patient 14 related to voiding, e.g., the inhibition of bladder contractions. In addition, in some examples, therapy system 30 may include a greater or fewer number of microstimulators 32 than that shown in FIG. 2, such as one or more than four.

In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, e.g., number and position of microstimulators, are possible.

Systems 10 and 30 shown in FIGS. 1 and 2, respectively, are merely examples of delivers stimulation therapy to generate an inhibitory physiological response in patient 14 to manage a bladder dysfunction of patient 14. Systems with other configurations of leads, electrodes, and sensors are possible. Additionally, in other examples, a system may include more than one IMD. For example, a system may include an IMD coupled to one or more leads for delivering a first stimulation therapy and another IMD coupled to one or more leads for delivering a second stimulation therapy. As another example, a therapy system can include one or more leadless electrical stimulators.

Figure 3:
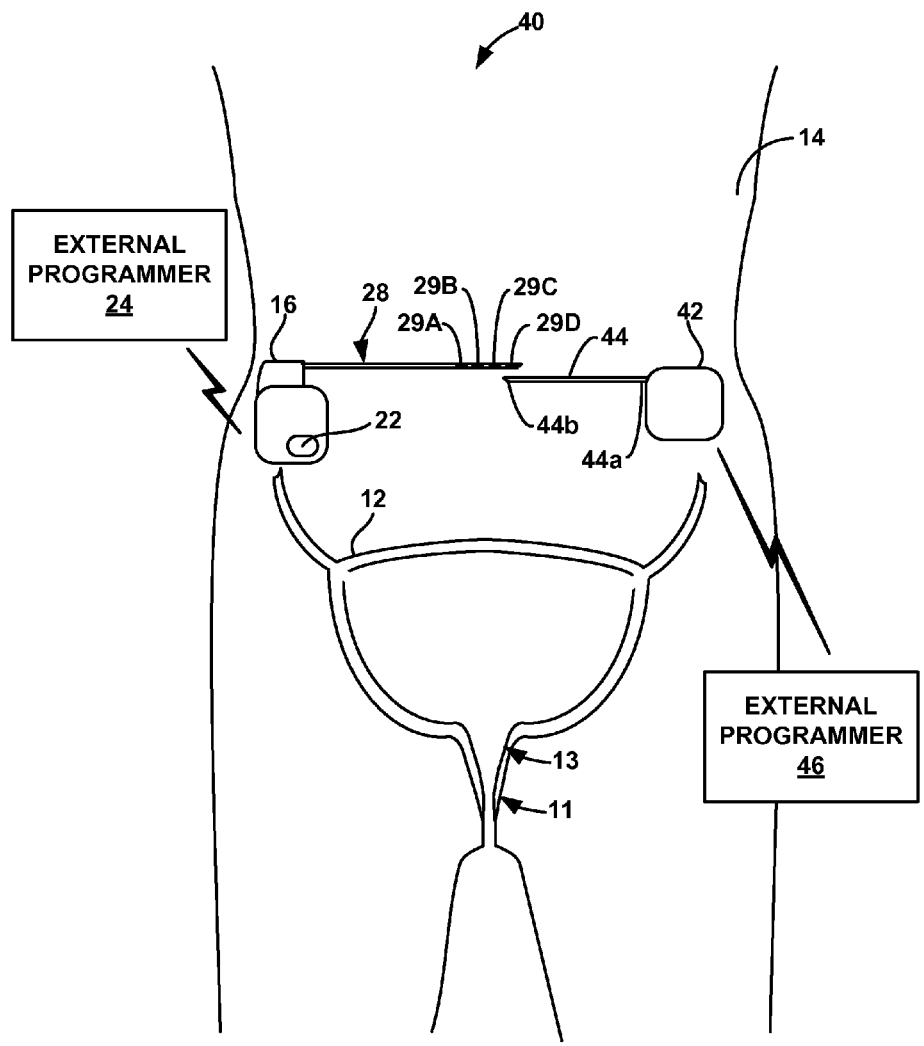
FIG. 3 is a conceptual diagram that illustrates an example therapy system that includes an IMD and an implantable drug delivery device.

FIG. 3 is a conceptual diagram that illustrates an example of a therapy system 40 that includes IMD 16 and an implantable drug delivery device 42. IMD 16 is mechanically and electrically coupled to lead 28, as described above with respect to FIG. 1. Lead 28 carries electrodes 29, which are electrically coupled to circuitry, such as a therapy delivery module, within IMD 16 via one or more conductors within lead 28. Implantable drug delivery device 42 is mechanically and fluidically coupled to catheter 44, and communicates wirelessly with external programmer 46. Implantable drug delivery device 42 is configured to deliver at least one pharmacological agent to a target site within patient 14 via catheter 44.

Implantable drug delivery device 42 includes an outer housing that, in some examples, is constructed of a biocompatible material that resists corrosion and degradation from bodily fluids including, e.g., titanium or biologically inert polymers. Implantable drug delivery device 42 may be implanted within a subcutaneous pocket relatively close to the therapy delivery site. For example, in the example shown in FIG. 3, implantable drug delivery device 42 is implanted within an abdomen of patient 14. In other examples, implantable drug delivery device 42 may be implanted within other suitable sites within patient 14, which may depend, for example, on the target site within patient 14 for the delivery of the pharmacological agent. In still other examples, a drug delivery device may be external to patient 14 with a percutaneous catheter connected between the drug delivery device and the target delivery site within patient 14.

Implantable drug delivery device 42 delivers a pharmacological agent from a reservoir (not shown) to patient 14 through catheter 44 from proximal end 44a coupled to IMD 16 to distal end 44b located proximate to the target site. Example pharmacological agents that may be delivered by implantable drug delivery device 42 include, e.g., VR1 (TRPV1) agonists in sufficiently high doses, VR1 (TRPV1) antagonists, capsaicin in sufficiently high doses, Na+ channel blockers, Ca++ channel blockers, botulinum toxin (e.g., Botox®), or the like. As used herein, "sufficiently high doses" refers to doses in sufficient quantities of active ingredient that C-afferent fibers are not activated to cause pain or discomfort in patient 14, but instead are desensitized. For example, at relatively low doses, capsaicin may activate C-afferent fibers and may cause pain or discomfort. In sufficiently high doses, capsaicin may desensitize C-afferent fibers. In some examples, whether a dose is sufficient high or not may be influenced by, for example, the manner and location of administration of the dose.

In some examples, implantable drug delivery device 42 may deliver the pharmacological agent to the target site to desensitize at least one C-afferent nerve fiber. As describe herein, desensitization of at least one C-afferent nerve fiber may provide synergistic therapeutic effects in combination with electrical stimulation therapy of a nerve that includes the desensitized C-afferent nerve fiber.

Catheter 44 can comprise a unitary catheter or a plurality of catheter segments connected together to form an overall catheter length. Catheter 44 may be coupled to IMD 16 either directly or with the aid of a catheter extension (not shown in FIG. 3). In the example shown in FIG. 3, catheter 44 traverses from the implant site of implantable drug delivery device 42 to a target therapy site proximate to electrodes 29. Catheter 44 is positioned such that one or more fluid delivery outlets (not shown in FIG. 3) of catheter 44 are proximate to the target therapy site within patient 14. In the example of FIG. 3, implantable drug delivery device 42 delivers a pharmacological agent through catheter 44 to the target therapy site proximate to electrodes 29.

As described above with respect to FIG. 1, in some examples, catheter 44 may be positioned such that one or more fluid delivery outlets (not shown in FIG. 3) of catheter 44 are located at a different site (a site other than the site to which IMD 16 delivers stimulation therapy) to administer the pharmacological agent. For example, catheter 44 may be positioned such that one or more fluid delivery outlets deliver the pharmacological agent to a nerve or nerves that innervates the target therapy site at a location other than within the target therapy site. For example, catheter 44 may be positioned such that one or more fluid delivery outlets deliver the pharmacological agent in a location either upstream or downstream of the target therapy site (e.g., in a direction in which electrical signals travel from in the nerve or in a direction in which electrical signals travel to in the nerve). In other examples, catheter 44 may be positioned such that one or more fluid delivery outlets deliver the pharmacological agent to a nerve other than the target nerve to which IMD 16 delivers stimulation therapy, where the other nerve may inadvertently be captured by stimulation delivery by IMD 16 to the target nerve. For example, catheter 44 may be positioned such that one or more fluid delivery outlets deliver the pharmacological agent intravesically (within bladder 12), intradetrusorally, epidurally, intrathecally.

As described with respect to FIG. 1, implantable drug delivery device 42 may administer (or deliver) the pharmacological agent according to at least one pharmacological therapy program. The pharmacological therapy program may define parameters according to which implantable drug delivery device 42 delivers the pharmacological agent. For example, the pharmacological therapy program may specify a schedule of different pharmacological agent delivery rates and/or other parameters by which the drug delivery device delivers the pharmacological agent to patient 14. As another example, the pharmacological therapy program may define a schedule of when implantable drug delivery device 42 delivers the pharmacological agent, e.g., when implantable drug delivery device 42 delivers the pharmacological agent to patient 14 periodically.

In other examples, implantable drug delivery device 42 delivers a pharmacological agent to patient 14 to desensitize a C-afferent nerve fiber in response to user input, which may be received by drug delivery device 42 or from IMD 16, programmer 46 or another device. For example, a user (e.g., patient 14, a patient caretaker, or a clinician) may provide input to programmer 46 to indicate C-afferent nerve fiber desensitization is desired, electrical stimulation is desired or one or more symptoms of urgency (e.g., bladder contractions) are perceived by patient 14, at which time, implantable drug delivery device 42 may deliver the pharmacological agent to patient 14. In this way, implantable drug delivery device 42 may deliver the pharmacological agent to patient 14 based on the delivery of stimulation therapy by IMD 16 or independent of the schedule with which IMD 16 delivers therapy to patient 14.

In general, a pharmacological therapy program stored on implantable drug delivery device 42 defines one or more pharmacological agent doses to be delivered from implantable drug delivery device 42 to patient 14. A dose of pharmacological agent may refer to a total amount of pharmacological agent, e.g., measured in milligrams or other volumetric units, delivered over a total amount of time, e.g., per day or twenty-four hour period. The amount of pharmacological agent in a dose may convey to patient 14 or a caregiver an indication of the probable efficacy of the agent and the possibility of side effects.

In general, a sufficient amount of the pharmacological agent should be administered in order to have a desired therapeutic effect, such as desensitization of at least one C-afferent nerve fiber. However, the amount of the pharmacological agent delivered to patient 14 should be limited to a maximum amount, such as a maximum daily amount, in order to limit or avoid potential side effects. Pharmacological therapy program parameters specified by a user, e.g., via programmer 46, may include fluid volume per dose, dose time period, and/or maximum dose for a given time interval, e.g., daily. In some examples, dosage may also prescribe particular concentrations of active ingredients in the pharmacological agent delivered by implantable drug delivery device 42 to patient 14.

The manner in which a dose of pharmacological agent is delivered to patient 14 by implantable drug delivery device 42 may also be defined in the therapy program. For example, a control module of implantable drug delivery device 42 may be programmed to deliver a dose of pharmacological agent according to a schedule that defines different rates at which the agent is to be delivered at different times during the dose period, e.g. a twenty-four hour period. The pharmacological agent rate refers to the amount, e.g. in volume, of pharmacological agent delivered over a unit period of time, which may change over the course of the dose period as implantable drug delivery device 42 delivers the dose of agent to patient 14.

In some examples, the pharmacological therapy program may include other parameters, including, e.g., time intervals between successive pharmacological agent doses. For example, implantable drug delivery device 42 may administered the pharmacological agent to patient 14 periodically. In some examples, the period may be determined, at least in part, by the duration for which the pharmacological agent desensitizes the C-afferent nerve fiber(s). For example, a pharmacological agent may desensitize the C-afferent nerve fiber(s) for a period of about one month. In such an example, implantable drug delivery device 42 pharmacological agent may be administered to patient 14 in approximately one-month intervals (e.g., intervals of slightly less than one month, such as 4 weeks) so the C-afferent nerve fiber(s) are substantially continuously desensitized. In other examples, the pharmacological agent may desensitize the C-afferent nerve fiber(s) for longer or shorter periods of time, and the frequency of administration of the pharmacological agent may accordingly be higher or lower. For example, implantable drug delivery device 42 may administer the pharmacological agent to patient 14 periodically, and the period may be measured in seconds, minutes, hours, days, months, years, decades, or the like.

In some examples, implantable drug delivery device 42 may administer the pharmacological agent substantially continuously to patient 14. As described above, implantable drug delivery device 42 may administer the pharmacological agent at a predetermined pharmacological agent rate (e.g., μL/h). In some examples, implantable drug delivery device 42 may administer the pharmacological agent truly continuously, e.g., via a peristaltic pump, while in other examples, implantable drug delivery device 42 may administer the pharmacological agent discontinuously or periodically, but the periods or discontinuities may be sufficiently short or small that the delivery may be considered substantially continuous. For example, implantable drug delivery device 42 may deliver the pharmacological agent periodically with a period that is measured in seconds or fractions of a second, or implantable drug delivery device 42 may deliver the pharmacological agent by a piston pump or other pump that delivers pulses of the pharmacological agent.

In some examples, implantable drug delivery device 42 may be configured to communicate with IMD 16, e.g., directly or via programmer 44 and/or programmer 46. For example, implantable drug delivery device 42 may communicate with IMD 16, programmer 44, and/or programmer 46 via wireless telemetry using any techniques known in the art. Examples of communication techniques may include, for example, low frequency or RF telemetry, but other techniques are also contemplated. In some examples, implantable drug delivery device 42 may communicate to IMD 16 an indication of administration of the pharmacological agent. As described above, IMD 16 may control delivery of stimulation therapy based on the indication received from implantable drug delivery device 42.

Programmer 46 is an external computing device that is configured to communicate with implantable drug delivery device 42 by wireless telemetry. For example, programmer 46 may be a clinician programmer that the clinician uses to communicate with implantable drug delivery device 42 and program therapy delivered by the implantable drug delivery device 42. Alternatively, programmer 46 may be a patient programmer that allows patient 14 to view and modify therapy parameters associated with therapy programs. The clinician programmer may include additional or alternative programming features than the patient programmer. For example, more complex or sensitive tasks may only be allowed by the clinician programmer to prevent patient 14 from making undesired or unsafe changes to the operation of implantable drug delivery device 42. Programmer 46 may be a handheld or other dedicated computing device, or a larger workstation or a separate application within another multi-function device.

Implantable drug delivery device 42 and programmer 46 may communicate via wireless communication using any techniques known in the art. Examples of communication techniques may include, for example, low frequency or RF telemetry, but other techniques are also contemplated. In some examples, programmer 46 may include a programming head that may be placed proximate to the patient's body near the implant site of implantable drug delivery device 42 in order to improve the quality or security of communication between implantable drug delivery device 42 and programmer 46.

Although external programmer 24 and external programmer 46 are illustrated and described as physically separate devices in FIG. 3, in some examples, a single programmer may include functionality ascribed separately to programmer 24 and programmer 46.

Additionally or alternatively, although implantable drug delivery device 42 and IMD 16 are illustrated and described as physically separate devices in FIG. 3 (e.g., enclosed in separate housings), in some examples, a single IMD (e.g., enclosed in a single housing) may include appropriate hardware, firmware, and/or software to implement the functions ascribed herein to both implantable drug delivery device 42 and IMD 16.

Figure 4:
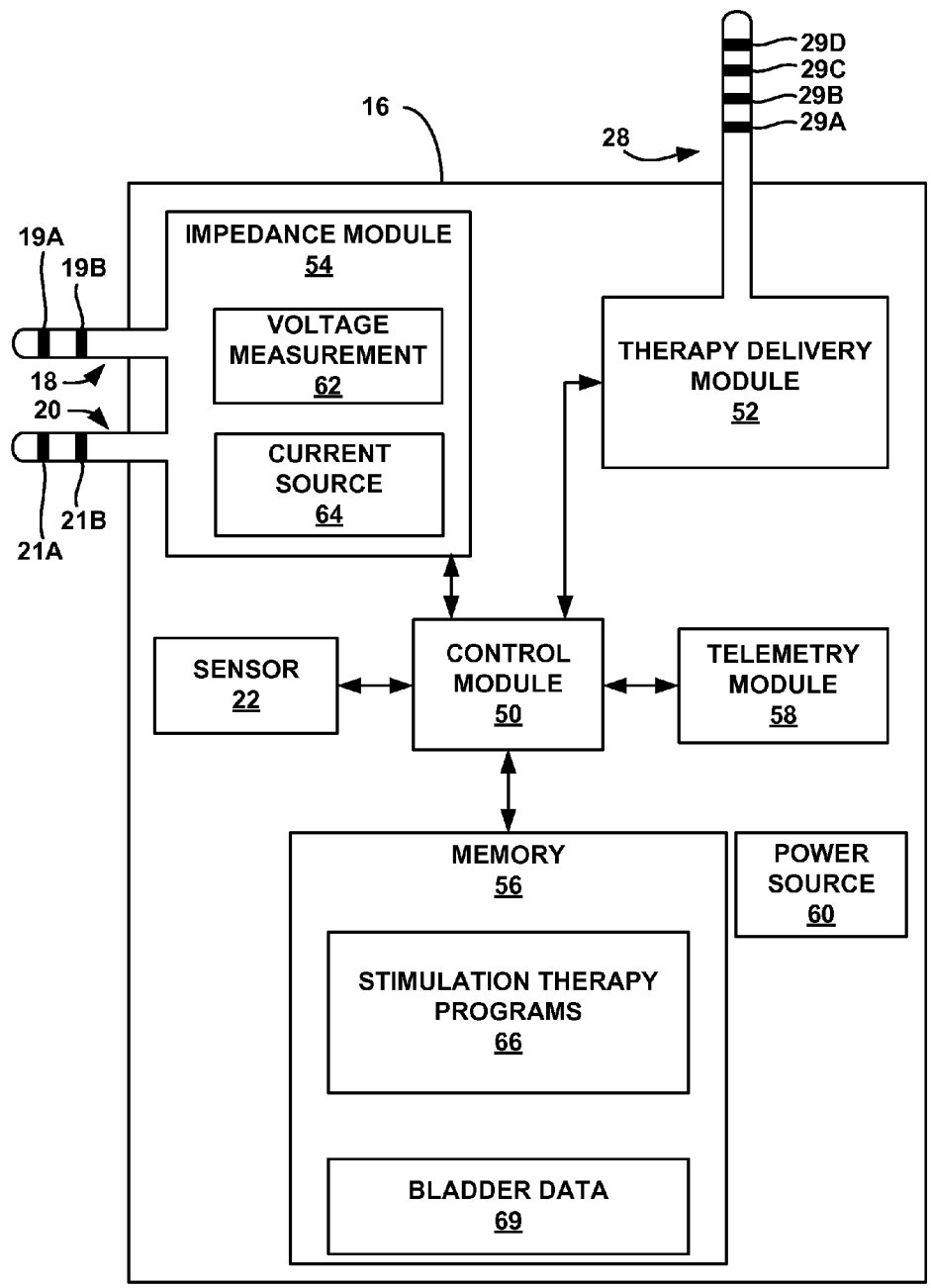
FIG. 4 is a functional block diagram that illustrates example components of an IMD that delivers electrical stimulation therapy to a patient to generate an inhibitory physiological response by the patient related to voiding.

FIG. 4 is a block diagram that illustrates example components of IMD 16. In the example of FIG. 4, IMD 16 includes sensor 22, control module 50, therapy delivery module 52, impedance module 54, memory 56, telemetry module 58, and power source 60. In other examples, IMD 16 may include a greater or fewer number of components. For example, in some examples, such as examples in which IMD 16 may deliver stimulation therapy in an open-loop manner, IMD 16 may not include sensor 22 and/or impedance module 54.

In general, IMD 16 comprises any suitable arrangement of hardware, alone or in combination with software and/or firmware, to perform the techniques attributed to IMD 16 and control module 50, therapy delivery module 52, impedance module 54, and telemetry module 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 56, such as any one or more of random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, or optical media comprising executable instructions for causing the one or more processors to perform the actions attributed to them. Moreover, although control module 50, therapy delivery module 52, impedance module 54, and telemetry module 58 are described as separate modules, in some examples, control module 50, therapy delivery module 52, impedance module 54, and telemetry module 58 are functionally integrated. In some examples, control module 50, therapy delivery module 52, impedance module 54, and telemetry module 58 correspond to individual hardware units, such as ASICs, DSPs, FPGAs, or other hardware units.

Memory 56 stores stimulation therapy programs 66 that specify stimulation parameter values for the stimulation therapy provided by IMD 16. In some examples, some of stimulation therapy programs 66 may be associated with a marker or indication that ties the respective one of programs 66 to whether the pharmaceutical agent was delivered to patient 14. In some examples, memory 56 may store one or more therapy programs 66 that define electrical stimulation therapy that is delivered when the C-afferent fibers are not desensitized (e.g., because the effects of a pharmacological agent that has such an effect have substantially dissipated or because the pharmacological agent has not been delivered). In some implementations, the therapy programs 66 may be grouped or otherwise indicated for use when the C-afferent fibers are not desensitized.

Additionally or alternatively, memory 56 may store one or more therapy programs 66 that define electrical stimulation therapy that is delivered when the C-afferent fibers are desensitized. In some implementations, the therapy programs 66 may be grouped or otherwise indicated for use when the C-afferent fibers are desensitized.

In other examples, memory 56 may store one or more therapy programs 66 that define electrical stimulation therapy that is delivered when the C-afferent fibers are desensitized or when the C-afferent fibers are not desensitized. In some implementations, the therapy programs 66 may not be grouped or otherwise indicated for use when the C-afferent fibers are desensitized or when the C-afferent fibers are not desensitized.

In some examples, memory 56 also stores bladder data 69, which control module 50 may use for controlling the stimulation parameters or timing of delivery of the stimulation therapy (e.g., in a closed-loop mode). For example, bladder data 69 may include threshold values or baseline values for at least one of bladder impedance, bladder pressure, sacral or pudendal afferent nerve signals, bladder contraction frequency, or external urinary sphincter EMG templates. As described in further detail below, the threshold values and baseline values may indicate a particular event, such as a bladder contraction or a condition indicative of a voiding-related physiological condition (e.g., a patient state in which there is a relatively high likelihood of an involuntary voiding event).

Memory 56 may also store instructions for execution by control module 50, in addition to stimulation therapy programs 66 and bladder data 69. Information related to sensed bladder contractions, bladder impedance and/or posture of patient 14 may be recorded for long-term storage and retrieval by a user, or used by control module 50 for adjustment of stimulation parameters, such as amplitude, pulse width, and pulse rate. In some examples, memory 56 includes separate memories for storing instructions, electrical signal information, stimulation therapy programs, and bladder data.

Generally, therapy delivery module 52 generates and delivers stimulation therapy under the control of control module 50. In some examples, control module 50 controls therapy delivery module 52 by accessing memory 56 to selectively access and load at least one of stimulation therapy programs 66 to therapy delivery module 52. For example, in operation, control module 50 may access memory 56 to load one of stimulation therapy programs 66 to therapy delivery module 52.

By way of example, control module 50 may access memory 56 to load one of stimulation therapy programs 66 to therapy delivery module 52 for delivering electrical stimulation therapy to patient 14. A clinician or patient 14 may select a particular one of stimulation therapy programs 66 from a list using a programming device, such as programmer 24 or a clinician programmer. Control module 50 may receive the selection via telemetry module 58. Therapy delivery module 52 delivers the stimulation therapy to patient 14 according to the selected program for an extended period of time, such as hours, days, weeks, or until patient 14 or a clinician manually stops or changes the program. In some examples, the respective stimulation therapy programs 66 may define a schedule of first time periods ("on" periods) and second time periods ("off" periods), such that a stimulation signal is not continuously delivered to patient 14, but periodically delivered in accordance with predetermined parameters for the stimulation therapy. In other examples, control module 50 may determine the timing with which IMD 16 delivers stimulation to patient 14 according to different programs based on sensor input or patient input.

Therapy delivery module 52 delivers stimulation therapy, i.e., electrical stimulation, according to stimulation parameters. In some examples, therapy delivery module 52 delivers therapy in the form of electrical pulses. In such examples, relevant stimulation parameters may include a voltage amplitude, a current amplitude, a pulse rate, a pulse width, a duty cycle, or the combination of electrodes 29 therapy delivery module 52 uses to deliver the stimulation signal. In other examples, therapy delivery module 52 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 29 therapy delivery module 52 uses to deliver the stimulation signal.

In some examples, the stimulation parameters for the stimulation programs 66 may be selected to relax bladder 12, e.g., to reduce a frequency of contractions of bladder 12. An example range of stimulation parameters for the electrical stimulation therapy that are likely to be effective in treating bladder dysfunction, e.g., when applied to any one or more of the spinal, sacral, pudendal, tibial, dorsal genital, inferior rectal, or perineal nerves, are as follows:

1. Frequency or pulse rate: less than about 500 Hz, such as between about 0.5 Hz and about 500 Hz, less than about 250 Hz, less than about 60 Hz, between about 0.1 Hz and about 50 Hz, between about 0.1 Hz and about 20 Hz, or about 10 Hz.

2. Amplitude: using voltage amplitude as an example, between about 0.1 volts and about 50 volts, such as between about 0.5 volts and about 20 volts, or between about 1 volt and about 10 volts. An amplitude between about 0.1 volts and about 2 volts may elicit a delayed inhibitory physiological response from patient 14 (e.g., an inhibitory physiological response that is observed within about two minutes to about five minutes after the initiation of the stimulation therapy).

3. Pulse Width: between about 10 microseconds (μs) and about 5000 μs, such as between about 100 μs and about 1000 μs, or between about 180 μs and about 450 μs.

Additionally, in some examples in which control module 50 controls the delivery of stimulation to patient 14 according to a schedule of first time periods ("on" periods) and second time periods ("off" periods), the stimulation parameters may include a duration of the first time period and a duration of the second time period. In some examples, the duration of the first time period is at least five minutes, such as between about five minutes and about 20 minutes, or about 10 minutes. In other words, in some examples, therapy delivery module 52 delivers stimulation to patient 14 via electrodes 29 for a duration of at least five minutes, such as between about five minutes and about 20 minutes or about 10 minutes.

In some examples the duration of the second period, during which therapy delivery module 52 does not deliver the stimulation therapy to patient 14, is at least five minutes, such as between five minutes and about 30 minutes or between about 10 minutes and about 20 minutes.

In some examples, the stimulation parameter values are selected from among those listed above such that the stimulation therapy elicits a first inhibitory physiological response related to voiding of patient 14 during the first time period and a second physiological response (e.g., an inhibition of a physiological function, such as bladder contractions, related to involuntary voiding) related to voiding of patient 14 during the second time period. In some examples, the stimulation parameters are selected such that the stimulation therapy elicits substantially no inhibitory physiological response related to voiding of patient 14 during the first time period. In other words, the physiological response of patient 14 may be substantially similar during the first time period and during a time period prior to the first time period during which therapy delivery module 52 delivers stimulation therapy to patient 14. In some examples, the first and second inhibitory physiological responses related to voiding include a reduction in contraction frequency of bladder 12 (FIG. 1).

In some examples, the stimulation therapy delivered to patient 14 by therapy delivery module 52 elicits a second physiological response related to voiding of patient 14 during the second time period which, for at least a portion of the second time period, is greater than the first physiological response of patient 14. For example, a contraction frequency of bladder 12 during at least a portion of the second time period may be lower than a contraction frequency of bladder 12 during the first time period. In this way, the stimulation therapy delivered by therapy delivery module 52 elicits a post-stimulation inhibitory effect that extends beyond the first time period, into the second time period.

In some examples, at least some of stimulation therapy programs 66 may define a stimulation intensity that is less than, equal to, or greater than a threshold stimulation intensity. As described above, the threshold stimulation intensity may be defined as the stimulation intensity at which a physiological response of patient 14 is first observed when increasing the stimulation intensity from a relatively low intensity to a higher intensity.

In some implementations, control module 50 may determine the threshold intensity by setting stimulation parameters (e.g., a current amplitude, a voltage amplitude, a frequency or pulse rate, a pulse width, a shape, a duty cycle, and/or the combination of electrodes 29) to produce a relatively low stimulation intensity and controlling therapy delivery module 52 to deliver stimulation to patient 14 via electrodes 29 using these stimulation parameter values. If no physiological response is detected or observed, control module 50 may change one stimulation parameter automatically or in response to an input received from a user via programmer 24 and telemetry module 58, while the remaining parameters are kept approximately constant, and control module 50 may control therapy delivery module 52 to deliver stimulation at the new stimulation intensity. This may be repeated until a physiological response is detected or observed. When stimulating one of the nerves described herein, such as a spinal nerve, sacral nerve, pudendal nerve, or the like, the observed or detected physiological response may be a contraction of a toe of patient 14, a flexing of an anal sphincter of patient 14, or a detected signal on an electromyography (EMG). The physiological response may be observed by patient 14 or a clinician or may be detected by sensor 22 or electrodes 19, 21 coupled to IMD 16. Other physiological responses may be detected when stimulating other nerves of patient 14.

In some examples, once the threshold intensity is determined, control module 50 may define a therapy program, automatically or in response to an input received from a clinician via programmer 24 and telemetry module 58. The therapy program may be stored as one of stimulation therapy programs 66 in memory 56. In some examples, the therapy program may include stimulation parameters that define a stimulation intensity that is between about 50% (half) and about 300% (three times) the threshold intensity, such as about 75% of the threshold intensity. In some implementations, the therapy program may include stimulation parameters that define a stimulation intensity that is between about 50% and about 100% of the threshold stimulation intensity, such as about 75% of the threshold intensity. In other implementations, the therapy program may include stimulation parameters that define a stimulation intensity that is between about 100% and about 300% of the threshold intensity.

Control module 50 can change the stimulation intensity from the threshold intensity by adjusting a value of at least one of the stimulation parameters described above, such as, for example, a current amplitude, a voltage amplitude, a frequency or pulse rate, a pulse width, a signal shape, a duty cycle, or the combination of electrodes 29. For example, the current and/or voltage amplitude of the stimulation signal may be reduced to reduce an intensity of the stimulation signal or may be increased to increase an intensity of the stimulation signal.

In some examples, at least some of stimulation therapy programs 66 may define values for a set of stimulation parameters, including in some implementations the durations of the first and second time periods, which cause therapy delivery module 52 to deliver stimulation therapy to patient 14 in an open loop manner. In such cases, therapy delivery module 52 delivers stimulation to patient 14 according to the same stimulation parameters, without controlling the stimulation therapy in response to a sensed physiological parameter or an input from patient 14. In some examples, therapy delivery module 52 continues to deliver stimulation therapy to patient 14 according to these stimulation parameters until receiving an instruction from control module 50 to interrupt therapy delivery. In some examples, control module 50 may issue such an instruction to therapy delivery module 52 in response to receiving an input for a user, such as a clinician, via telemetry module 58.

In some examples, at least one of stimulation therapy programs 66 defines stimulation parameters that cause therapy delivery module 52 to deliver stimulation therapy to patient 14 in a closed loop manner. In closed loop stimulation therapy, therapy delivery module 52, under the control of control module 50, may deliver stimulation therapy to patient based on at least one feedback signal, e.g., a signal representative of a physiological response of patient 14 sensed by at least one of sensor 22, electrodes 19, or electrodes 21. For example, control module 50 may control therapy delivery module 52 to adjust the delivery of stimulation (e.g., to initiate the delivery of stimulation or increase or decrease the value of a stimulation parameter) based on fullness state of bladder 12, which may be determined based on an impedance determined across bladder 12 via electrodes 19, 21. As another example, control module 50 or therapy delivery module 52 may control delivery of stimulation therapy by therapy delivery module 52 based on a contraction frequency of bladder 12. In some examples, the control of stimulation therapy delivery by control module 50 or therapy delivery module 52 may include controlling a stimulation parameter with which therapy delivery module 52 generates the stimulation signal.

To facilitate delivery of stimulation in a closed loop manner, the at least one of stimulation therapy programs 66 may include a baseline contraction frequency or a threshold contraction frequency. The baseline contraction frequency may be contraction frequency of bladder 12 at a time prior to delivery of stimulation therapy by therapy delivery module 52. For example, the baseline contraction frequency of bladder 12 may be sensed and determined by control module 50 after implantation of IMD 16 in patient 14, but before therapy delivery module 52 delivers any stimulation therapy to patient 14. In some examples, the baseline contraction frequency of bladder 12 may represent the patient state when no therapeutic effects from delivery of stimulation by IMD 16 are present.

Control module 50 may determine the baseline contraction frequency of bladder 12 utilizing signals representative of physiological parameters received from at least one of sensor 22, electrodes 19 or electrodes 21. In some examples, control module 50 monitors impedance of bladder 12 to detect contraction of bladder 12 based on signals received from impedance module 54. For example, control module 50 may determine an impedance value based on signals received from impedance module 54 and compare the determined impedance value to a threshold impedance value stored in memory 56 as bladder data 69. When the determined impedance value is less than the threshold value stored in bladder data 69, control module 50 detects bladder contraction. In some implementations, control module 50 monitors impedance of bladder 12 for a predetermined duration of time to detect contractions of bladder 12, and determines the baseline contraction frequency of bladder 12 by determining a number of contractions of bladder 12 in the predetermined duration of time.

In the example illustrated in FIG. 4, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, control module 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Control module 50 determines an impedance value from the measure voltage values received from voltage measurement circuitry 52.

In other examples, control module 50 may monitor signals received from sensor 22 to detect contraction of bladder 12 and determine the baseline contraction frequency. In some examples, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12. In some implementations, control module 50 monitors pressure of bladder 12 to detect contractions of bladder 12 for a predetermined duration of time, and determines a contraction frequency of bladder 12 by calculating a number of contractions of bladder 12 in the predetermined time period.

In some examples, control module 50 causes the baseline contraction frequency to be stored in bladder data 69, and utilizes the baseline contraction frequency when delivering stimulation therapy in a closed loop manner. In other examples, control module 50 may cause a threshold contraction frequency to be stored as bladder data 69 in memory 56, and may utilize the threshold contraction frequency when delivering stimulation therapy in a closed loop manner, e.g., to determine when to deliver stimulation therapy to patient 14 according to a particular therapy program. In some implementations, control module 50 may, automatically or under control of a user, determine the threshold contraction frequency based on a baseline contraction frequency. For example, control module 50 may determine the threshold contraction frequency as a predetermined percentage of the baseline contraction frequency or a percentage of the baseline contraction frequency input by a user via programmer 24. As one example, the threshold frequency may be between approximately 75% and approximately 100% of the baseline contraction frequency.

In some examples, the threshold contraction frequency may not be based on a baseline contraction frequency of patient 14, and may instead be based on clinical data collected from a plurality of patients. For example, the threshold contraction frequency may be determined based on an average bladder contraction frequency of a plurality of patients during a bladder filling time period, i.e., during a time period in which the plurality patients are not experiencing a voluntary or involuntary voiding event. In any case, the threshold contraction frequency may be stored in bladder data 69, and, in some examples, control module 50 may utilize the threshold contraction frequency when delivering stimulation therapy in a closed loop manner to patient 14.

In other examples, instead of utilizing a threshold contraction frequency or a baseline contraction frequency, control module 50 may control closed-loop delivery of stimulation therapy based on an EMG template. In some implementations, sensor 22 may include an EMG sensor, and control module 50 may generate an EMG from the received signals generated by sensor 22. Sensor 22 may be implanted proximate to a muscle which is active when bladder 12 is contracting, such as a detrusor muscle. Control module 50 may compare an EMG signal collected during the second time period to EMG templates stored as bladder data 69 to determine whether the contractions of bladder 12 indicate a return to a baseline contraction frequency or pattern. In some cases, control module 50 may generate the EMG template based on received signals generated by sensor 22 after implantation of IMD 16, but before therapy delivery module 52 delivers any stimulation therapy to patient 14.

Control module 50, then, may utilize at least one of a threshold contraction frequency, a baseline contraction frequency, or a template EMG to control therapy delivery module 52 to deliver stimulation therapy in a closed loop manner. For example, control module 50 may monitor impedance of bladder 12 to detect contraction of bladder 12 based on signals received from impedance module 54. In some implementations, control module 50 substantially continuously monitors impedance of bladder 12 to detect contraction of bladder 12, and determines a contraction frequency of bladder 12 by determining a number of contractions of bladder 12 in a specified time period.

In other examples, sensor 22 may be a pressure sensor and control module 50 may monitor signals received from sensor 22 to detect contraction of bladder 12. In some implementations, control module 50 substantially continuously monitors pressure of bladder 12 to detect contraction of bladder 12, and determines a contraction frequency of bladder 12 by determining a number of contractions of bladder 12 in a specified time period.

After determining a contraction frequency of bladder 12, control module 50 may compare the determined contraction frequency of bladder 12 to the threshold contraction frequency stored in memory 56 as bladder data 69. When the determined contraction frequency is greater than or substantially equal to the threshold contraction frequency stored in bladder data 69, control module 50 may control therapy delivery module 52 to initiate or modify delivery of stimulation therapy to patient 14. For example, in implementations in which therapy delivery module 52 generates and delivers stimulation therapy that includes a plurality of interleaved first and second time periods, control module 50 may end the second time period and initiate the first time period based on the determined contraction frequency being greater than or equal to the threshold contraction frequency.

In other examples, control module 50 may compare the determined contraction frequency of bladder 12 and the baseline contraction frequency to determine a difference between the determined contraction frequency and the baseline contraction frequency. In some examples, when the difference is less than or equal to a specified value (e.g., a threshold difference value), control module 50 may cause therapy delivery module 52 to initiate or modify delivery of stimulation therapy to patient 14. For example, in implementations in which therapy delivery module 52 generates and delivers stimulation therapy that includes a plurality of interleaved first and second time periods, control module 50 may end the second time period and initiate the first time period based on the determined contraction frequency being greater than or equal to the threshold contraction frequency.

In other examples, sensor 22 may include an EMG sensor, and control module 50 may generate an EMG from the received signals generated by sensor 22 (e.g., which may sense the muscle activity with one or more sensor positioned near the target muscle) and compare the EMG to an EMG template stored as bladder data 69 to determine whether the contractions of bladder 12 are indicative of a predetermined characteristic which causes control module 50 to control therapy delivery module 52 to initiate or modify delivery of the stimulation therapy. For example, the predetermined characteristic may be a frequency of contractions of bladder, an amplitude of the signal (representative of intensity of contractions of bladder 12), or the like.

In some implementations, closed loop therapy may allow control module 50 and therapy delivery module 52 to deliver more efficacious therapy to patient 14 by controlling the delivery of the stimulation to respond to a specific physiological state (e.g., a bladder contraction frequency level) of patient 14. For example, based on the determined contraction frequency of bladder 12, control module 50 may cause therapy delivery module 52 to modify at least one stimulation parameter according to which therapy delivery module 52 delivers of stimulation therapy to patient 14. For example, control module 50 may cause therapy delivery module 52 to initiate delivery of stimulation therapy to patient 14 prior to the end of the second time period specified in the selected one of stimulation therapy programs 66. In this manner, closed loop therapy may reduce or substantially eliminate an amount of time that a contraction frequency of bladder 12 is at a baseline level (e.g., a level substantially similar to the contraction frequency of bladder 12 prior to delivery of any stimulation therapy).

As discussed above, in some examples, delivery of stimulation during the first time period may generate a delayed physiological response that may help prevent the occurrence of an involuntary voiding event, whereby the physiological response is more pronounced during at least a portion of the second time period that follows the first time period. Thus, by timing the delivery of the stimulation to occur prior to observation of the baseline bladder contraction frequency, control module 50 may help time therapy such that there is sufficient time for the first therapy (delivered during the first time period) to generate the desired physiological response. In some examples, the first time period during which the stimulation is delivered to patient 14 is selected to generate the desired physiological response (e.g., a particular percentage of bladder contraction frequency or a particular bladder contraction frequency value) during the second time period. The delivery of the stimulation by therapy module 52 may not generate an acute physiological response in patient 14 that may help reduce the possibility of an occurrence of an involuntary voiding event, but, rather, such physiological response may be observed after delivering the stimulation for some minimum period of time, which may be less than or equal to the first time period.

Generally, control module 50 controls telemetry module 58 to exchange information with medical device programmer 24 (FIG. 1) and/or another device external to IMD 16. Control module 50 may transmit operational information and receive stimulation programs or stimulation parameter adjustments via telemetry module 58. Telemetry module 58 includes any suitable hardware, firmware, software or any combination thereof for communicating with another device, such as programmer 24. Under the control of control module 50, telemetry module 58 may receive downlink telemetry, e.g., patient input, from and send uplink telemetry, e.g., device data, to programmer 24 with the aid of an antenna, which may be internal and/or external. Control module 50 may provide the data to be uplinked to programmer 24 and the control signals for the telemetry circuit within telemetry module 58, and receive data from telemetry module 58. Also, in some examples, IMD 16 may communicate with other implanted devices, such as stimulators, control devices, or sensors, via telemetry module 58.

Examples of local wireless communication techniques that may be employed by telemetry module 58 to facilitate communication between control module 50 of IMD 16 and another computing device, such as programmer 24 (FIGS. 1-3), implantable drug delivery device 42 (FIG. 3), or programmer 46 (FIG. 3) include RF communication according to the 802.11 or Bluetooth specification sets, or other standard or proprietary telemetry protocols.

As previously described, in some examples, control module 50 may receive an indication (e.g., via telemetry module 58) that a pharmacological agent has been administered to patient 14, e.g., by a clinician or via implantable drug delivery device 42. In some examples, the indication may be input by a user, such as a clinician or patient 14, via programmer 24 upon administration of the pharmacological agent to patient 14. Programmer 24 then may transmit the indication to control module 50 via telemetry module 58. In other examples, implantable drug delivery device 42 or an implantable drug delivery module that may be substantially enclosed in the outer housing of IMD 16 with therapy delivery module 52 may automatically generate and transmit the notification to control module 50 via telemetry module 58 upon administering the pharmacological agent to patient 14.

In some examples, control module 50 may select one of stimulation therapy programs 66 based on the based on the received indication. For example, control module 50 may select one of stimulation therapy programs 66 that includes stimulation parameters that define a higher stimulation intensity than control module 50 would otherwise select if the pharmacological agent had not been administered to patient 14. As described above, in some examples, desensitization of the C-afferent nerve fiber(s) by the pharmacological agent may facilitate use of a higher, efficacious stimulation intensity by reducing discomfort or pain experienced by patient 14 due to the stimulation therapy. In other examples, control module 50 may select one of stimulation therapy programs 66 that includes stimulation parameters that define a relatively lower stimulation intensity (e.g., within a range of stimulation intensities which control module 50 would select when the pharmacological agent had not been administered to patient 14). As described above, in some examples, C-afferent fiber(s) that innervate bladder 12 may promote contraction of bladder 12, thus inhibiting an efficacy of the stimulation therapy when the C-afferent fiber(s) are activated. In some examples, desensitization of the C-afferent fiber(s) may therefore increase an efficacy of the stimulation therapy delivered by therapy delivery module 52. Control module 50 may then control therapy delivery module 52 to generate and deliver the stimulation therapy to patient 14 in accordance with the selected one of stimulation therapy programs 66.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 5:
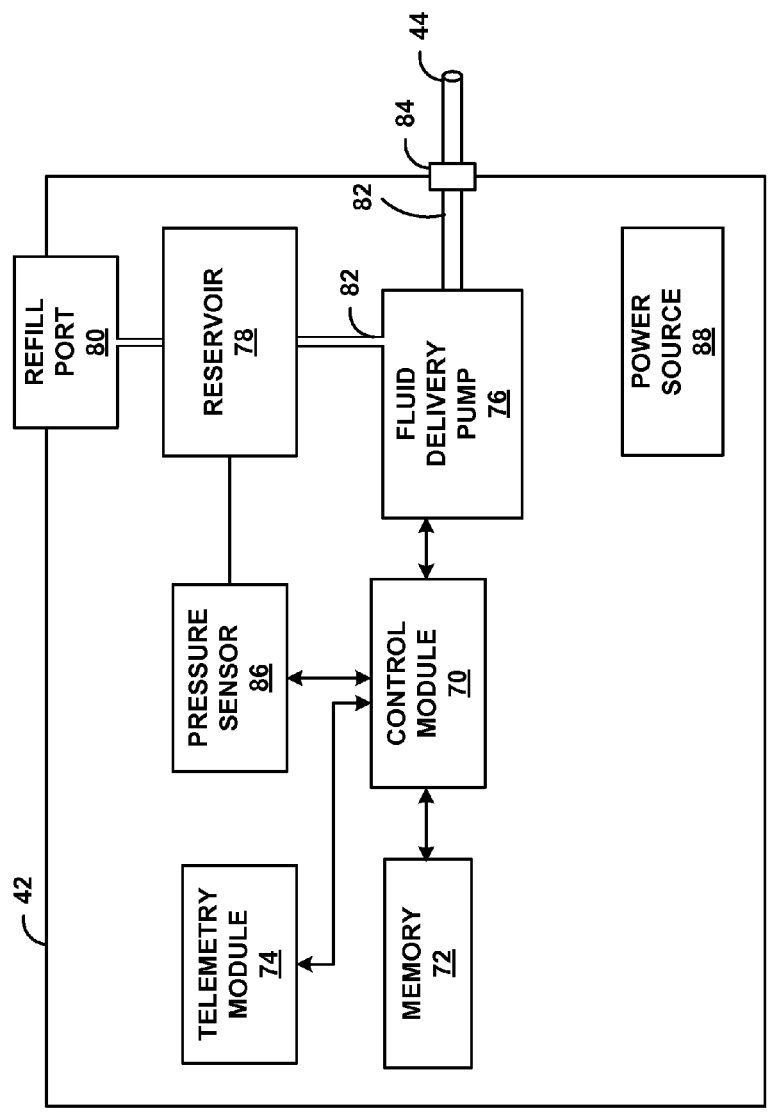
FIG. 5 is a functional block diagram that illustrates components of an example implantable drug delivery device.

FIG. 5 is a functional block diagram that illustrates components of an example implantable drug delivery device 42, which includes control module 70, memory 72, telemetry module 74, fluid delivery pump 76, reservoir 78, refill port 80, internal tubing 82, catheter access port 84, pressure sensor 86 and power source 88. Control module 70 is communicatively connected to memory 72, telemetry module 74, and fluid delivery pump 76. Fluid delivery pump 76 is fluidly connected to reservoir 78 and internal tubing 82. Reservoir 78 is fluidically connected to refill port 80. Catheter access port 84 is fluidically connected to internal tubing 82 and catheter 44.

In general, implantable drug delivery device 42 comprises any suitable arrangement of hardware, alone or in combination with software and/or firmware, to perform the techniques attributed to implantable drug delivery device 42 and control module 70 and telemetry module 74 of implantable drug delivery device 42. In various examples, implantable drug delivery device 42 may include one or more processors, such as one or more microprocessors, DSPs, ASICs, FPGAs, or any other equivalent integrated or discrete logic circuitry, as well as any combinations of such components. Implantable drug delivery device 42 also, in various examples, may include a memory 72, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although control module 70 and telemetry module 74 are described as separate modules, in some examples, control module 70 and telemetry module 74 are functionally integrated. In some examples, control module 70 and telemetry module 74 correspond to individual hardware units, such as ASICs, DSPs, FPGAs, or other hardware units.

In general, memory 72 stores program instructions and related data that, when executed by control module 70, cause implantable drug delivery pump 42 and control module 70 to perform the functions attributed to them in this disclosure. For example, memory 72 may store instructions for execution by control module 70 including, e.g., therapy programs, programs for monitoring the volume of pharmacological agent in reservoir 78, and any other information regarding therapy delivered to patient 14 and/or the operation of implantable drug delivery device 42. Memory 72 may include separate memories for storing instructions, patient information, pharmacological therapy parameters, therapy adjustment information, program histories, and other categories of information such as any other data that may benefit from separate physical memory modules. Therapy adjustment information may include information relating to timing, frequency, rates and amounts of boluses or other permitted patient modifications to therapy.

In some examples, implantable drug delivery device 42 may include a plurality of reservoirs 78 for storing more than one type of pharmacological agent. In some examples, implantable drug delivery device 42 may include a single long tube that contains the pharmacological agent in place of reservoir 78. However, for ease of description, an implantable drug delivery device 42 that includes a single reservoir 78 is primarily described with reference to the disclosed examples.

During operation of implantable drug delivery device 42, control module 70 controls fluid delivery pump 76 with the aid of instructions associated with program information (e.g., pharmacological therapy programs) that is stored in memory 72 to deliver a pharmacological agent to patient 14 via catheter 44. Instructions executed by control module 70 may, for example, define therapy programs that specify the dose of pharmacological agent that is delivered to a target tissue site within patient 14 from reservoir 78 via catheter 44. The programs may further specify a schedule of different pharmacological agent rates and/or other parameters, such as a periodic dose schedule, by which implantable drug delivery device 42 delivers the pharmacological agent to patient 14.

In general, a pharmacological therapy program stored in memory 72 and executed by control module 70 defines one or more pharmacological agent doses to be delivered from reservoir 78 to patient 14 through catheter 44 by implantable drug delivery device 42. A dose of pharmacological agent generally refers to a total amount of pharmacological agent, e.g., measured in milligrams or other volumetric units, delivered over a total amount of time, e.g., per day or twenty-four hour period. The amount of pharmacological agent in a dose may convey to a caregiver an indication of the probable efficacy of the agent and the possibility of side effects.

In general, a sufficient amount of the pharmacological agent should be administered in order to have a desired therapeutic effect, such as desensitization of at least one C-afferent nerve fiber. However, the amount of the pharmacological agent delivered to patient 14 can be limited to a maximum amount, such as a maximum daily amount, in order not to avoid potential side effects. Therapy program parameters specified by a user, e.g., via programmer 46 (FIG. 3) may include fluid volume per dose, dose time period, maximum dose for a given time interval, e.g., daily. In some examples, dosage may also prescribe particular concentrations of active ingredients in the pharmacological agent delivered by implantable drug delivery device 42 to patient 14.

The manner in which a dose of pharmacological agent is delivered to patient 14 by implantable drug delivery device 42 may also be defined in the therapy program. For example, control module 70 of implantable drug delivery device 42 may be programmed to deliver a dose of pharmacological agent according to a schedule that defines different rates at which the agent is to be delivered at different times during the dose period, e.g. a twenty-four hour period. The pharmacological agent rate refers to the amount, e.g., in volume, of pharmacological agent delivered over a unit period of time, which may change over the course of a day as implantable drug delivery device 42 delivers the dose of fluid to patient 14.

The pharmacological therapy program may include other parameters, including, e.g., time intervals between successive pharmacological agent doses. For example, control module 70 may control fluid delivery pump 76 to administer the pharmacological agent to patient 14 periodically. In some examples, the period may be determined, at least in part, based on the duration for which the pharmacological agent desensitizes the C-afferent nerve fiber(s). For example, a certain dosage of a particular pharmacological agent may desensitize the C-afferent nerve fiber(s) for a period of about one month. In such an example, control module 70 may control fluid delivery pump 76 to administer the pharmacological agent to patient 14 at the determined dosage in approximately one-month intervals (e.g., intervals of slightly less than one month, such as 4 weeks or exactly one month) so the C-afferent nerve fiber(s) are substantially continuously desensitized. In other examples, a certain dosage of the pharmacological agent may desensitize the C-afferent nerve fiber (s) for longer or shorter periods of time, and the frequency of administration of the pharmacological agent may accordingly be higher or lower. For example, control module 70 may control fluid delivery pump 76 to administer the pharmacological agent to patient 14 periodically, and the period may be measured in seconds, minutes, hours, days, months, years, decades, or the like.

In some examples, control module 70 may control fluid delivery pump 76 to administer the pharmacological agent substantially continuously to patient 14. As described above, control module 70 may control fluid delivery pump 76 to administer the pharmacological agent at a predetermined pharmacological agent rate (e.g., μL/h). In some examples, control module 70 may control fluid delivery pump 76 to administer the pharmacological agent truly continuously, e.g., via a peristaltic pump, while in other examples, control module 70 may control fluid delivery pump 76 to administer the pharmacological agent discontinuously or periodically, but the periods or discontinuities may be sufficiently short or small that the delivery may be considered substantially continuous. For example, control module 70 may control fluid delivery pump 76 to deliver the pharmacological agent periodically with a period that is measured in seconds or fractions of a second, or control module 70 may control fluid delivery pump 76 to deliver the pharmacological agent by a piston pump or other pump that delivers pulses of the pharmacological agent.

Pharmacological therapy programs may be a part of a program group, where the group includes a number of pharmacological therapy programs. Memory 72 may store one or more pharmacological therapy programs, as well as instructions defining the extent to which patient 14 may adjust therapy parameters, switch between pharmacological therapy programs, or undertake other therapy adjustments. Patient 14 or a clinician may select and/or generate additional pharmacological therapy programs for use by control module 70, e.g., via external programmer 46 at any time during therapy or as designated by the clinician.

Upon instruction from control module 50, fluid delivery pump 76 draws the pharmacological agent from reservoir 78 and pumps the agent through internal tubing 82 to catheter 44 through which the agent is delivered to patient 14. Internal tubing 82 may be a segment of tubing or a series of cavities within implantable drug delivery device 42 that runs from reservoir 78, around or through fluid delivery pump 76, and to catheter access port 84.

Fluid delivery pump 76 can be any mechanism that delivers a pharmacological agent in some metered or other desired flow dosage to the therapy site (e.g., a C-afferent nerve fiber) within patient 14 from reservoir 78 via implanted catheter 44. In one example, fluid delivery pump 76 is a squeeze pump that squeezes internal tubing 82 in a controlled manner, e.g., such as a peristaltic pump, to progressively move fluid from reservoir 78 to the distal end of catheter 44 and then into patient 14 according to parameters specified by the pharmacological therapy program stored in memory 72 and executed by control module 70.

In various examples, fluid delivery pump 76 may be an axial pump, a centrifugal pump, a pusher plate pump, a piston-driven pump, or other means for moving the pharmacological agent through internal tubing 82 and catheter 44. In one example, fluid delivery pump 76 is an electromechanical pump that delivers fluid by the application of pressure generated by a piston that moves in the presence of a varying magnetic field and that is configured to draw the pharmacological agent from reservoir 78 and pump the pharmacological agent through internal tubing 82 and catheter 44 to patient 14.

Implantable drug delivery device 42 may include pressure sensor 86, which is configured to measure pressure in reservoir 78. Pressure sensor 86 may be arranged in a number of locations within implantable drug delivery device 42 including, e.g., in reservoir 78 or refill port 80. Regardless of where arranged, pressure sensor 86 is communicatively connected to control module 70 to transmit pressure-related information to the control module 70 for analysis and storage in memory 72 in order to, e.g., determine the actual rate at which pharmacological agent is delivered from reservoir 78 to patient 14, and/or the actual volume of pharmacological agent remaining in the reservoir 78.

Pressure sensor 86 may be electronically coupled to control module 70, or a control module of another device, in a variety of ways including electrical wiring (not shown) or a wireless link between the pressure sensor 86 and the processing device. Pressure sensor 86 may be any device capable of measuring pressure of reservoir 78. For example, pressure sensor 86 may be a capacitive measurement device which determines pressure by measuring the change in capacitance of a flexible membrane attached but insulated from a conductive, gas-filled cavity due to deflections caused by pressure applied over the flexible membrane (i.e., a capacitive pressure sensor). Alternatively, pressure sensor 86 may be a sensor that utilizes the piezo-electric effect (i.e., a piezo-electric pressure sensor) or resistive change due to metallic strain (i.e., a strain gauge pressure sensor) in order to measure pressure applied.

Control module 70, alone or in conjunction with a processor of programmer 46 (FIG. 3) or another device communicatively connected to implantable drug delivery device 42, may be configured to receive the pressure of reservoir 78 measured by pressure sensor 86. In some examples, control module 70 may also be configured to control an ambulatory volume gauge to indicate to patient 14 or another user the volume of pharmacological agent in reservoir 78 as the implantable drug delivery device 42 delivers the pharmacological agent to patient 14. In one example, control module 70 is configured to determine a volume of pharmacological agent in reservoir 34 based on changes in the pressure of the reservoir measured by pressure sensor 42 over time. Control module 70 also may control an ambulatory fluid volume gauge to indicate the determined volume of fluid in reservoir 78, e.g., via programmer 46 (FIG. 3).

Periodically, after implantation of device 42 in patient 14, pharmacological agent may need to be supplied percutaneously to reservoir 78 because all of a pharmacological agent has been or will be delivered to patient 14, or because a clinician wishes to replace an existing fluid with a different fluid or similar fluid with different concentrations of active ingredients. In some examples, refill port 80 comprises a self-sealing membrane to prevent loss of therapeutic fluid delivered to reservoir 78 via refill port 80. For example, after a percutaneous delivery system, e.g., a hypodermic needle, penetrates the membrane of refill port 80, the membrane may self-seal when the needle is removed from refill port 80.

At various times during the operation of implantable drug delivery device 42 to treat patient 14, communication to and from implantable drug delivery device 42 may be necessary to, e.g., change pharmacological therapy programs, adjust parameters within one or more pharmacological therapy programs, configure or adjust a particular bolus, transmit an indication regarding delivery of the pharmacological agent to programmer 46 or IMD 16, or to otherwise download information to or from implantable drug delivery device 42. Control module 70 controls telemetry module 74 to wirelessly communicate with programmer 46 (FIG. 3) and other devices including, e.g., IMD 16.

Telemetry module 74 in implantable drug delivery device 42, as well as telemetry modules in other devices described in this disclosure, such as programmer 24, programmer 46, or IMD 16, can be configured to use RF communication techniques to wirelessly send and receive information to and from other devices respectively according to, e.g., the 802.11 or Bluetooth specification sets, infrared (IR) communication according to the IRDA specification set, or other standard or proprietary telemetry protocols. In addition, telemetry module 74 may communicate with programmer 46 and/or IMD 16 via proximal inductive interaction between implantable drug delivery device 42 and the external programmer 46 and/or IMD 16. Telemetry module 74 may send information to external programmer 46 and/or IMD 16 on a continuous basis, at periodic intervals, or upon request from the programmer 46 or IMD 16.

In some examples, control module 70 may control telemetry module 74 to communicate to control module 50 of IMD 16 or to one or both programmers 24, 46 (FIG. 3) an indication of administration of the pharmacological agent. As described above, control module 50 of IMD 16 may control delivery of stimulation therapy based on the indication received from implantable drug delivery device 42 or one or both programmers 24, 26.

Power source 88 delivers operating power to various components of implantable drug delivery device 42. Power source 88 may include a small rechargeable or non-rechargeable battery and a power generation circuit to produce the operating power. In the case of a rechargeable battery, recharging may be accomplished through proximal inductive interaction between an external charger and an inductive charging coil within implantable drug delivery device 42. In some examples, power requirements may be small enough to allow implantable drug delivery device 42 to utilize patient motion and implement a kinetic energy-scavenging device to trickle charge a power source 88 that includes a rechargeable battery. In other examples, traditional batteries may be used for a limited period of time. As another alternative, an external inductive power supply could transcutaneously power implantable drug delivery device 42 as needed or desired.

Although described as physically separate devices (e.g., enclosed in separate housings), in some examples, implantable drug delivery device 42 and IMD 16 may be implemented in a single device, e.g., may share a common housing. In some examples, the various functionalities, e.g., at least one of control modules 50, 70, telemetry modules 58, 74, therapy delivery module 52, impedance module 54, may be implemented in one or more processors, such as DSPs, ASICs, FPGAs, or any other equivalent integrated or discrete logic circuitry, as well as any combinations of such components. Similarly, memories 56, 72, may include physically separate memory devices or may include one or more combined memory device that stores information described herein. Moreover, although control modules 50,70, therapy delivery module 52, impedance module 54, and telemetry modules 58, 74 are described as separate modules, in some examples, at least some of control modules 50, 70, therapy delivery module 52, impedance module 54, and telemetry modules 58, 74 may be functionally integrated.

Figure 6:
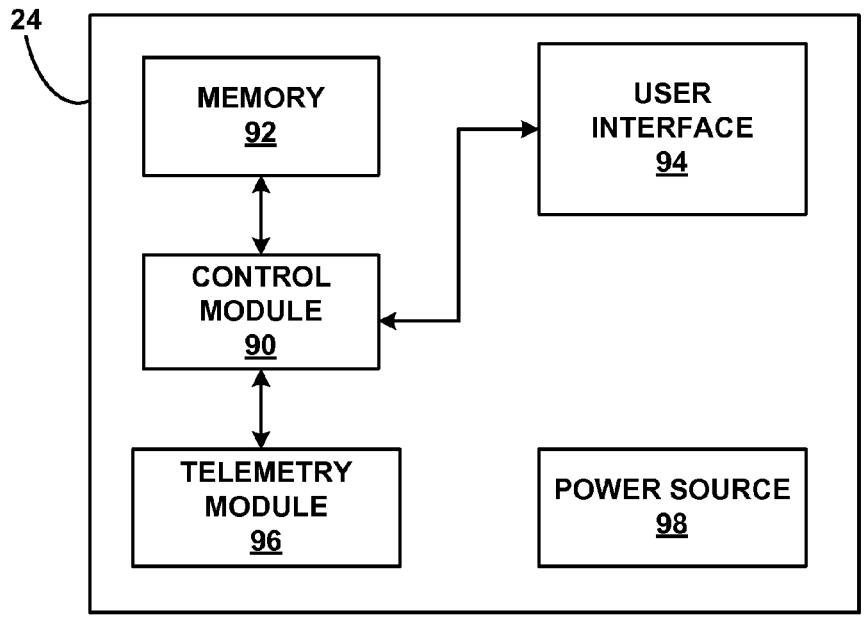
FIG. 6 is a functional block diagram that illustrates example components of an external programmer for communicating with an IMD.

FIG. 6 is a block diagram illustrating example components of external programmer 24. While programmer 24 may generally be described as a hand-held computing device, the programmer 24 may be a notebook computer, a cell phone, or a workstation, for example. As illustrated in FIG. 6, external programmer 24 may include a control module 90, memory 92, user interface 94, telemetry module 96, and power source 98. Memory 92 may store program instructions that, when executed by control module 90, cause control module 90 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and control module 90, user interface 94, and telemetry module 96 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 92, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although control module 90 and telemetry module 96 are described as separate modules, in some examples, control module 90 and telemetry module 96 are functionally integrated. In some examples, control module 90 and telemetry module 96 correspond to individual hardware units, such as ASICs, DSPs, FPGAs, or other hardware units.

Memory 92 may store program instructions that, when executed by control module 90, cause control module 90 and programmer 24 to provide the functionality ascribed to programmer 24 throughout this disclosure. In some examples, memory 92 may further include program information, e.g., therapy programs defining the stimulation therapy provided by IMD 16, similar to those stored in memory 56 of IMD 16. The stimulation programs stored in memory 92 may be downloaded into memory 56 of IMD 16.

User interface 94 may include a user input mechanism configured to receive input from a patient, such as a button or keypad, lights, a speaker for voice commands, a display, such as a LCD, LED, OLED, or CRT. In some examples the display may be a touch screen. As discussed in this disclosure, control module 90 may present and receive information relating to stimulation therapy via user interface 94. For example, control module 90 may receive patient input via user interface 94. The input may be, for example, in the form of pressing a button on a keypad or selecting an icon from a touch screen.

Control module 90 may also present information to the patient in the form of alerts related to delivery of the stimulation therapy to patient 14 or a caregiver, as will be described in more detail below, via user interface 94. Although not shown, programmer 24 may additionally or alternatively include a data or network interface to another computing device, to facilitate communication with the other device, and presentation of information relating to first and second stimulation therapies via the other device.

Telemetry module 96 supports wireless communication between programmer 24 and another device, such as IMD 16 under the control of control module 90. Telemetry module 96 may also be configured to communicate with another computing device, such as programmer 46, via wireless communication techniques, or direct communication through a wired connection. Telemetry module 96 may be substantially similar to telemetry module 58 described above, providing wireless communication via an RF or proximal inductive medium. In some examples, telemetry module 96 may include an antenna, which may take on a variety of forms, such as an internal or external antenna. Examples of local wireless communication techniques that may be employed to facilitate communication between programmer 24 and another computing device include RF communication according to the IEEE 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the stimulation therapy that generates an inhibitory physiological response to manage bladder dysfunction. If programmer 24 controls the stimulation, programmer 24 may transmit therapy programs for implementation by control module 50 to IMD 16 via telemetry module 96. A user (e.g., patient 14 or a clinician) may select the stimulation therapy programs from a list provided via a display of user interface 94. Additionally or alternatively, programmer 24 may transmit a signal to IMD 16 indicating that control module 50 should execute locally stored therapy programs or therapy routines. In such a manner, control over the electrical stimulation may be distributed between IMD 16 and external programmer 24, or may reside in either one alone.

Power source 98 delivers operating power to the components of programmer 24. Power source 98 may include a battery and a power generation circuit to produce the operating power. In some examples, the battery may be rechargeable to allow extended operation. Recharging may be accomplished by electrically coupling power source 98 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 98 may include circuitry to monitor power remaining within a battery. In this manner, user interface 94 may provide a current battery level indicator or low battery level indicator when the battery needs to be replaced or recharged. In some cases, power source 98 may be capable of estimating the remaining time of operation using the current battery.

In some examples, programmer 24 may include a user interface element, e.g., a user interface screen, a button, or the like, via a display of user interface 94 that allows a user to input an indication that a pharmacological agent that desensitizes at least one C-afferent fiber of patient 14 has been administered to patient 14. In some implementations, control module 90 may present a user interface element or screen via user interface 94 that allows the user, such as a clinician or patient 14, to input the indication. In some examples, the clinician introduce the pharmacological agent, e.g., transcutaneously via a hypodermic needle, to a target site proximate a nerve or branch of a nerve that is targeted for stimulation therapy by IMD 16. As another example, the clinician may introduce the pharmacological agent intravesically (in bladder 12), e.g., transcutaneously via a hypodermic needle.

Control module 90 may be configured to receive the indication from the user via user interface 94 and may be configured to control telemetry module 96 to transmit the indication to control module 50 of IMD 16 via telemetry module 58 of IMD 16. In some examples, control module 50 may control delivery of stimulation therapy to patient 14 based on the indication, e.g., control module 50 may select one or more stimulation therapy programs 66 (FIG. 4) based on the indication.

In other examples, control module 90 may receive an indication from another device, such as implantable drug delivery device 42 (FIGS. 3 and 5) or programmer 46 (FIG. 3) that the pharmacological agent that desensitizes at least one C-afferent fiber of patient 14 has been administered to patient 14. For example, control module 70 of implantable drug delivery device 42 (FIG. 5) may control fluid delivery pump 76 to deliver the pharmacological agent to patient 14 via catheter 44. In some examples, control module 70 may then control telemetry module 74 of implantable drug delivery device 42 to transmit the indication of the delivery of the pharmacological agent to control module 90 of programmer 24 directly via telemetry module 96. In other examples, control module 70 may control telemetry module 74 of implantable drug delivery device 42 to transmit the indication of the delivery of the pharmacological agent to control module 50 of IMD 16 via the respective telemetry modules 74, 68 (FIGS. 4 and 5).

In other examples, control module 70 may control telemetry module 74 of implantable drug delivery device 42 to transmit the indication of the delivery of the pharmacological agent to control module 102 of programmer 46 (FIG. 7) via telemetry module 108. Control module 102 of programmer 46 then may control telemetry module 108 to transmit the indication to control module 90 of programmer 24 via telemetry module 96. Regardless, once control module 90 of programmer 24 receives the indication that implantable drug delivery device 42 has administered the pharmacological agent to patient 14, control module 90 may cause telemetry module 96 to transmit the indication to control module 50 of IMD 16 (FIG. 4) automatically or under control of a user, such as a clinician or patient 14 (e.g., via user interface 94). Control module 50 of IMD 16 may control therapy delivery module 52 (FIG. 4) to deliver stimulation therapy to patient 14 based on the indication, e.g., control module 50 may select one or more stimulation therapy programs 66 (FIG. 4) based on the indication.

Figure 7:
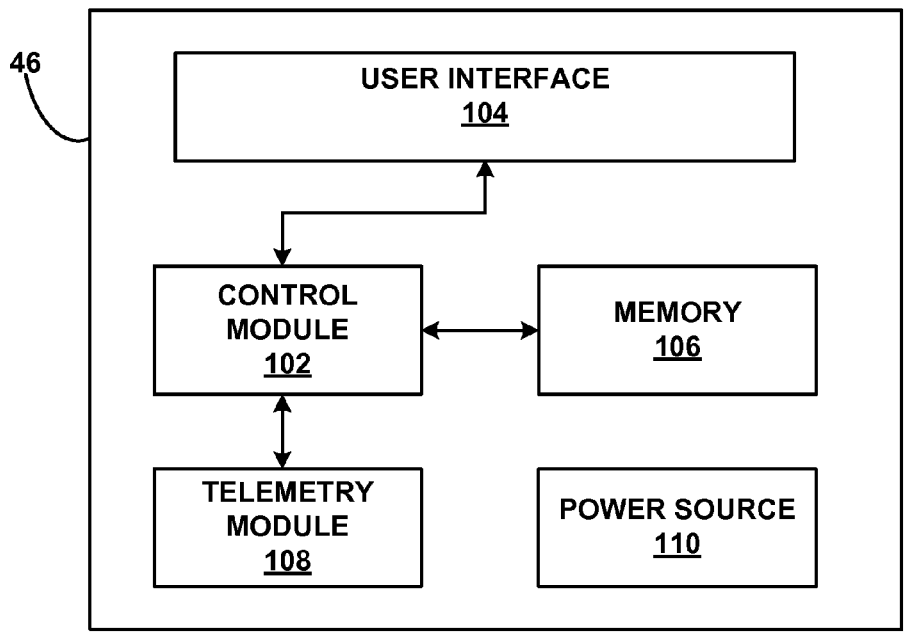
FIG. 7 is a functional block diagram that illustrates example components of an external programmer for communicating with an implantable drug delivery device.

FIG. 7 is a functional block diagram illustrating an example of various components of external programmer 46 for implantable drug delivery device 42. As shown in FIG. 7, external programmer 46 may include control module 102, user interface 104, memory 106, telemetry module 108, and power source 110.

External programmer 46 comprises any suitable arrangement of hardware, alone or in combination with software and/or firmware, to perform the techniques attributed to external programmer 46, and control module 102, user interface 104, and telemetry module 108 of external programmer 46. In various examples, external programmer 46 may include one or more processors, such as one or more microprocessors, DSPs, ASICs, FPGAs, or any other equivalent integrated or discrete logic circuitry, as well as any combinations of such components. External programmer 46 also, in various examples, may include a memory 106, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although control module 102 and telemetry module 108 are described as separate modules, in some examples, control module 102 and telemetry module 108 are functionally integrated. In some examples, control module 102 and telemetry module 108 correspond to individual hardware units, such as ASICs, DSPs, FPGAs, or other hardware units.

A clinician or patient 14 may interact with user interface 104 in order to manually change the parameters of a pharmaceutical agent therapy program, change therapy programs within a group of programs, view therapy information, view historical or establish new therapy programs, or otherwise communicate with implantable drug delivery device 42 or view or edit programming information. Control module 102 is configured to control user interface 104, retrieve data from memory 106, and store data within memory 106. Control module 102 is also configured to control the transmission of data through telemetry module 108 to and from implantable drug delivery device 42 or another device, such as programmer 24 for IMD 16 or with IMD 16 directly. The transmitted data may include, for example, therapy program information specifying various pharmacological agent delivery parameters. Memory 106 may store, e.g., operational instructions for control module 102 and data related to therapy for patient 14.

External programmer 46 may be a hand-held computing device that includes user interface 104, with which a user may interact to provide input to programmer 46. For example, programmer 46 may include a display screen that presents information to the user and a keypad, buttons, a peripheral pointing device, touch screen, voice recognition, or another input mechanism that allows the user to navigate though user interface 104 of programmer 46 and provide input. In other examples, rather than being a handheld computing device or a dedicated computing device, programmer 46 may be a larger workstation or a separate application within another multi-function device.

User interface 104 is configured to receive input from a user and may include, for example, a display screen or other output mechanisms and buttons or other input mechanisms that allow a user to receive information from and provide input to external programmer 46, respectively. In one example, user interface 104 includes one or more of a touch pad, increase and decrease buttons, an emergency shut off button, and other buttons needed to control the therapy delivered to patient 14 by implantable drug delivery device 42. In another example, user interface 104 may additionally or only utilize a touch screen display including, e.g., LCD, dot matrix display, OLED display, CRT display, touch screen, or any other device capable of delivering and/or accepting information. For visible indications of therapy program parameters or operational status, a display screen may suffice. For audible and/or tactile indications of therapy program parameters or operational status, programmer 46 may further include one or more audio speakers, voice synthesizer chips, piezoelectric buzzers, or the like.

In some examples, user interface 104 may be configured to present pharmacological therapy program information to the user, e.g., in the form of graphical bar graphs or charts, numerical spread sheets, or in any other manner in which information may be displayed. Further, user interface 104 may present nominal or suggested pharmacological therapy parameters that the user may accept via user interface 104. User interface 104 also provides input mechanisms to enable the user to program implantable drug delivery device 42 in accordance with one or more pharmacological therapy programs or otherwise provide data to implantable drug delivery device 42 necessary for delivering the pharmacological agent to patient 14.

When programmer 46 is configured for use by a clinician, user interface 104 may be used to transmit initial programming information to implantable drug delivery device 42 including hardware information for system 40 (FIG. 3), e.g., the type of catheter 44, the position of catheter 44 within patient 14, a baseline orientation of at least a portion of implantable drug delivery device 42 (such as refill port 80) relative to a reference point, and software information related to pharmacological agent delivery and operation of implantable drug delivery device 42, e.g., pharmacological therapy parameters of pharmacological therapy programs stored within implantable drug delivery device 42 or within programmer 46, the type and amount, e.g., by volume of therapeutic fluid(s) delivered by implantable drug delivery device 42 and any other information the clinician desires to program into implantable drug delivery device 42. The clinician may use programmer 46 during a programming session to define one or more pharmacological therapy programs by which implantable drug delivery device 42 delivers the pharmacological agent to patient 14, in which case patient 14 may provide feedback to the clinician during the programming session as to efficacy of a program being evaluated or desired modifications to the program. Programmer 46 may assist the clinician in the creation/identification of pharmacological therapy programs by providing a methodical system of identifying potentially beneficial therapy parameter values.

Programmer 46 may also be configured for use by patient 14. In some examples, when configured as a patient programmer, programmer 46 may have limited functionality in order to prevent patient 14 from altering critical functions or applications that may be detrimental to patient 14. In this manner, programmer 46 may only allow patient 14 to adjust certain pharmacological therapy parameters or set an available range for a particular therapy parameter that defines the delivery of the pharmacological agent to patient 14. In some cases, a patient programmer may permit the patient to control implantable drug delivery device 42 to deliver a supplemental, patient bolus, if permitted by the applicable therapy program administered by the implantable drug delivery device 42, e.g., if delivery of a patient bolus would not violate a lockout interval or maximum dosage limit. Programmer 46 may also provide an indication to patient 14 when therapy is being delivered or when implantable drug delivery device 42 needs to be refilled or when the power source within programmer 46 or implantable drug delivery device 42 need to be replaced or recharged.

In the example of FIG. 7, user interface 104 of programmer 46, whether employed as a patient or clinician programmer, may include an ambulatory volume gauge (not shown), which is configured to indicate the volume of pharmacological agent in reservoir 78 of implantable drug delivery device 42 (FIG. 5). Whether controlled by control module 70 of implantable drug delivery device 42, as described above, or control module 102 of programmer 46, the ambulatory volume gauge is configured to display via user interface 104 the volume of pharmacological agent in reservoir 78 that is determined based on changes in the pressure of the reservoir 78 (FIG. 5) measured by pressure sensor 86 (FIG. 5) over time.

In some examples, control module 102 of programmer 46 may be employed, in conjunction with or in lieu of control module 70 of implantable drug delivery device 42, to determine a volume of pharmacological agent in reservoir 78 based on changes in the pressure of the reservoir 78 measured by pressure sensor 86 over time and to control the ambulatory fluid volume gauge of user interface 104 to indicate the determined volume of agent in reservoir 78. In some examples, control module 70 of implantable drug delivery device 42 determines the volume of pharmacological agent in reservoir 78 and transmits the determined volume via telemetry module 74 to programmer 46. Control module 102 of programmer 46 may store the volume in memory 106. In other examples, however, control module 102 may query implantable drug delivery device 42 via telemetry module 108 to retrieve pressure measurements of reservoir 78 made by pressure sensor 86 and then determine the volume of pharmacological agent in the reservoir 78 based pressure changes measured by the pressure sensor 86. In either case, control module 102 of programmer 46 may store the volume in memory 106.

Telemetry module 108 allows the transfer of data to and from programmer 46 and implantable drug delivery device 42, as well as other devices, such as programmer 24, e.g. according to the RF communication techniques described above with reference to FIGS. 4-6. Telemetry module 108 may communicate automatically with implantable drug delivery device 42 at a scheduled time or when the telemetry module 108 detects the proximity of implantable drug delivery device 42. Alternatively, telemetry module 108 may communicate with implantable drug delivery device 42 when signaled by a user through user interface 104. To support RF communication, telemetry module 108 may include appropriate electronic components, such as amplifiers, filters, mixers, encoders, decoders, and the like. Programmer 46 may also communicate with programmer 24 or computing device via a wired or wireless connection using any of a variety of communication techniques, and/or via exchange of removable media, including, e.g., magnetic or optical disks, or memory cards or sticks including, e.g., non-volatile memory. Further, programmer 46 may communicate with implantable drug delivery device 42 or another device via, e.g., a local area network (LAN), wide area network (WAN), public switched telephone network (PSTN), or cellular telephone network, or any other terrestrial or satellite network appropriate for use with programmer 46 and implantable drug delivery device 42.

In some examples, programmer 46 may serve as an intermediary communication device between two other devices, such as, for example, implantable drug delivery device 42 and IMD 16 and/or programmer 24. For example, control module 70 of implantable drug delivery device 42 may control fluid delivery pump 76 to deliver the pharmacological agent to patient 14 via catheter 44. In some examples, control module 70 may then control telemetry module 74 of implantable drug delivery device 42 to transmit an indication of the delivery of the pharmacological agent to control module 102 of programmer 46 via telemetry module 108. Control module 102 of programmer 46 then may control telemetry module 108, either automatically or under control of a user, such as a clinician or patient 14, to transmit the indication to control module 90 (FIG. 6) of programmer 24 via telemetry module 96 or to control module 50 of IMD 16 via telemetry module 58 (FIG. 4). When control module 102 controls telemetry module 108 to transmit the indication to control module 90 of programmer 24, control module 90 may cause telemetry module 96 to transmit the indication to control module 50 (FIG. 4) of IMD 16 automatically or under control of a user. Regardless of how control module 50 receives the indication, control module 50 may control delivery of stimulation therapy to patient 14 based on the indication, e.g., control module 50 may select one or more stimulation therapy programs 66 (FIG. 4) based on the indication.

Power source 110 may be a rechargeable battery, such as a lithium ion or nickel metal hydride battery. Other rechargeable or conventional primary cell batteries may also be used. In some cases, external programmer 46 may be used when coupled to an AC outlet, i.e., AC line power, either directly or via an AC/DC adapter.

In some examples, external programmer 46 may be configured to recharge implantable drug delivery device 42 in addition to programming device 42. Alternatively, a recharging device may be capable of communication with implantable drug delivery device 42. Then, the recharging device may be able to transfer programming information, data, or any other information described herein to implantable drug delivery device 42. In this manner, the recharging device may be able to act as an intermediary communication device between external programmer 46 and implantable drug delivery device 42.

Although programmer 24 for IMD 16 and programmer 46 for implantable drug delivery device 42 have been illustrated and described as physically separate devices, in some examples, a single device may include hardware, software, and/or firmware than allows the device to provide functionality described herein of both programmer 24 and programmer 46. In such examples, the single programmer may be configured to communicate with both IMD 16 and implantable drug delivery device 42.

Figure 8:
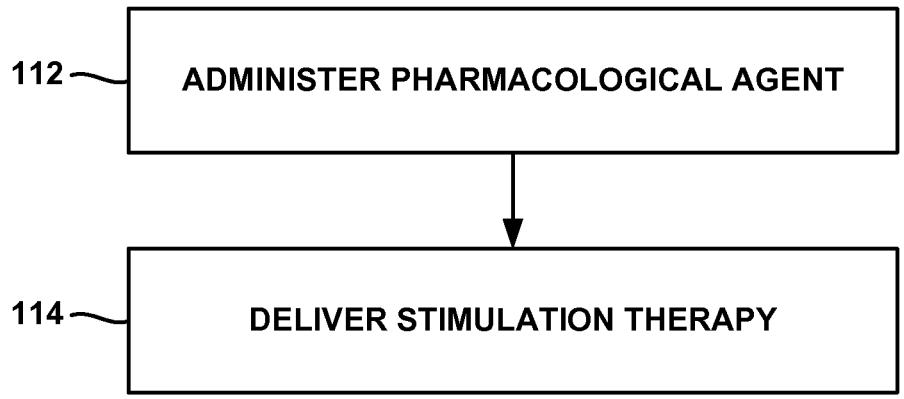
FIG. 8 is a flow diagram that illustrates an example technique that may be implemented to provide stimulation therapy to generate an inhibitory physiological response related to voiding in a patient.

FIG. 8 is a flow diagram that illustrates an example technique that may be implemented for providing stimulation therapy to generate an inhibitory physiological response by patient 14 related to voiding. Initially, a pharmacological agent is administered to patient 14 (112). As described above, the pharmacological agent may be delivered to a target site and in a dosage sufficient to desensitize at least one C-afferent nerve fiber of patient 14. The C-afferent nerve fiber(s) may be, for example, the C-afferent nerve fiber(s) of the same nerve to which IMD 16 delivers electrical stimulation therapy to generate an inhibitory physiological response related to voiding or part of a different nerve than the nerve to which IMD 16 delivers electrical stimulation. The pharmacological agent may be administered via one or more of a variety of administration methods, such as, for example, oral introduction, intravesical (in bladder 12) introduction, intradetrusor introduction, intrathecal introduction, epidural introduction, via an implantable drug delivery device 42, or the like.

As described above, in some examples, the pharmacological agent may be administered to patient 14 prior to a time period during which IMD 16 delivers stimulation to the nerve fiber. In addition, or instead, the pharmacological agent may be administered to patient 14 during delivery of stimulation to the nerve by IMD 16. In addition, as discussed above, in some examples, the pharmacological agent may be administered to patient 14 in a single dose or a single dose cycle prior to beginning delivery of stimulation therapy to patient 14 by IMD 16. In other examples, the pharmacological agent may be administered to patient 14 periodically. In some examples, the period may be determined, at least in part, by the duration for which the pharmacological agent desensitizes the at least one C-afferent nerve fiber. The pharmacological agent may be administered at regular intervals, e.g., periodically, irregular intervals, or substantially continuously, e.g., via an external or drug delivery device. In some examples, the pharmacological agent may be administered substantially continuously, e.g., via an external or implantable drug delivery device 42 according to at least one pharmacological therapy program.

In some examples, the pharmacological agent may be administered to patient 14 so that C-afferent nerve fibers(s) are substantially desensitized in the nerve targeted for stimulation therapy by IMD 16, e.g., so that C-afferent nerve fiber (s) are desensitized in a nerve or nerves located in or near the target therapy site (e.g., proximate to electrodes 29). For example, the pharmacological agent may be administered to patient 14 to desensitize C-afferent nerve fiber(s) in a location either upstream or downstream of the target therapy site (e.g., in a direction in which electrical signals travel from in the nerve or in a direction in which electrical signals travel to in the nerve). In other examples, the pharmacological agent may be administered intravesically (within bladder 12) via drug delivery device 42 or automatically by another device, although this may also be done via transcutaneous injection administered by a clinician, patient 14 or patient caregiver.

Once or contemporaneously with a clinician or other caregiver or fluid delivery pump 76 of device 42 (FIG. 5), under the control of control module 70, has administered sufficient pharmacological agent to a target location in patient 14 to desensitize at least one C-afferent nerve fiber (112), IMD 16 may deliver electrical stimulation therapy to a target tissue site in patient 14 to manage bladder dysfunction of patient 14 (114). In some examples, IMD 16 may deliver electrical stimulation therapy to patient 14 using any of the techniques described above. The target tissue site may be a tissue site proximate the nerve that comprises the C-afferent nerve fiber (s) that is desensitized. The stimulation therapy may activate a nerve fiber in the tissue site. The activated nerve fiber may be different than the desensitized C-afferent nerve fiber(s). As described above, in some examples, the nerve that comprises the desensitized C-afferent nerve fiber(s) may also include the nerve fiber that is activated by the stimulation therapy or may be different than the nerve that includes the nerve fiber that is activated by the stimulation therapy. The nerve fiber that is activated by the stimulation therapy may include an afferent nerve fiber, such as an A-Beta (Aβ) afferent nerve fiber or an A-Delta (Aδ) afferent nerve fiber, may include an efferent nerve fiber, or may include both. In some examples, the nerve fiber that is activated by the stimulation therapy is an afferent nerve fiber (i.e., includes substantially only afferent nerve fiber and substantially no efferent nerve fiber). In other examples, the nerve fiber that is activated by the stimulation therapy is an efferent nerve fiber (i.e., includes substantially only efferent nerve fiber and substantially no afferent nerve fiber).

IMD 16 may deliver stimulation therapy via at least one of electrodes 29 according to a stimulation therapy program. In some examples, the stimulation therapy program according to which IMD 16 delivers therapy may define a first time period and a second time period. IMD 16 may deliver stimulation at a first stimulation intensity during the first time period(s) and may deliver stimulation at a second stimulation intensity that is less than the first stimulation intensity during the second time period(s) that immediately follow respective first time period(s). As described above, the second stimulation intensity may include substantially no stimulation intensity, i.e., in some examples, delivering stimulation at the second stimulation intensity may include ceasing delivery of stimulation during the second time period.

The stimulation therapy program may define a stimulation intensity which elicits a first inhibitory physiological response related to voiding of patient 14 during the first time period, while IMD 16 delivers the stimulation therapy. In some examples, the stimulation therapy elicits substantially no inhibitory physiological response related to voiding of patient 14 during the first time period. In other words, the physiological response of patient 14 during the first time period may be substantially unchanged from the physiological response of patient 14 prior to IMD 16 delivering any stimulation therapy 16. In some examples, the physiological response comprises a contraction frequency of bladder 12.

The stimulation therapy delivered by IMD 16 elicits a second inhibitory physiological response of patient 14 during a second time period immediately following the first time period, during which the IMD 16 does not deliver stimulation therapy to patient 14. The second inhibitory physiological response may also be related to voiding and, for at least a portion of the second time period, may be greater than the first inhibitory physiological response. For example, the contraction frequency of bladder 12 may be lower for at least a portion of the second time period compared to the bladder contraction frequency during the first time period. In this way, the electrical stimulation delivered by IMD 16 during the first time period may produce a post-stimulation inhibitory effect that extends beyond the first time period.

In some examples, the stimulation therapy program with which IMD 16 generates and delivers therapy to patient 14 may define a stimulation intensity which is less than, equal to, or greater than a threshold stimulation intensity, which, as described above, can be a physiological intensity threshold or a therapeutic intensity threshold. In some examples, IMD 16 once the threshold intensity is determined, the stimulation parameter values with which IMD 16 delivers stimulation to patient 14 (114) may be changed such that the therapy program defines a stimulation intensity that is between about 50% (half) and about 300% (three times) the threshold intensity.

In some examples, IMD 16 may deliver the stimulation therapy in an open loop manner, in which IMD 16 delivers stimulation according to the stimulation parameters and does not modify the stimulation parameters in response to a detected physiological parameter or input from patient 14. In other examples, IMD 16 may deliver the stimulation therapy in a closed loop manner, e.g., IMD 16 may control at least one stimulation parameter based on feedback received from a user, such as patient 14, or a physiological sensor. For example, IMD 16 may modify at least one parameter of the stimulation therapy when IMD 16 detects a contraction frequency of bladder 12 that exceeds a particular threshold.

In some examples, IMD 16 may deliver the stimulation therapy chronically, e.g., may only cease delivering stimulation when instructed to via programmer 24 by a user, such as patient 14 or a clinician. In some examples, the pharmacological agent may be administered periodically or substantially continuously to patient 14. Thus, in some examples, the steps of administering the pharmacological agent to patient 14 (112) and delivering stimulation therapy to patient 14 via IMD 16 (114) may at least partially overlap in time. Alternatively or additionally, the steps of administering the pharmacological agent to patient 14 (112) and delivering stimulation therapy to patient 14 via IMD 16 (114) may be repeated in an alternating manner, e.g., administer the agent (112), deliver electrical stimulation therapy (114), administer the agent (112), deliver stimulation therapy (114), et cetera.

Figure 9:
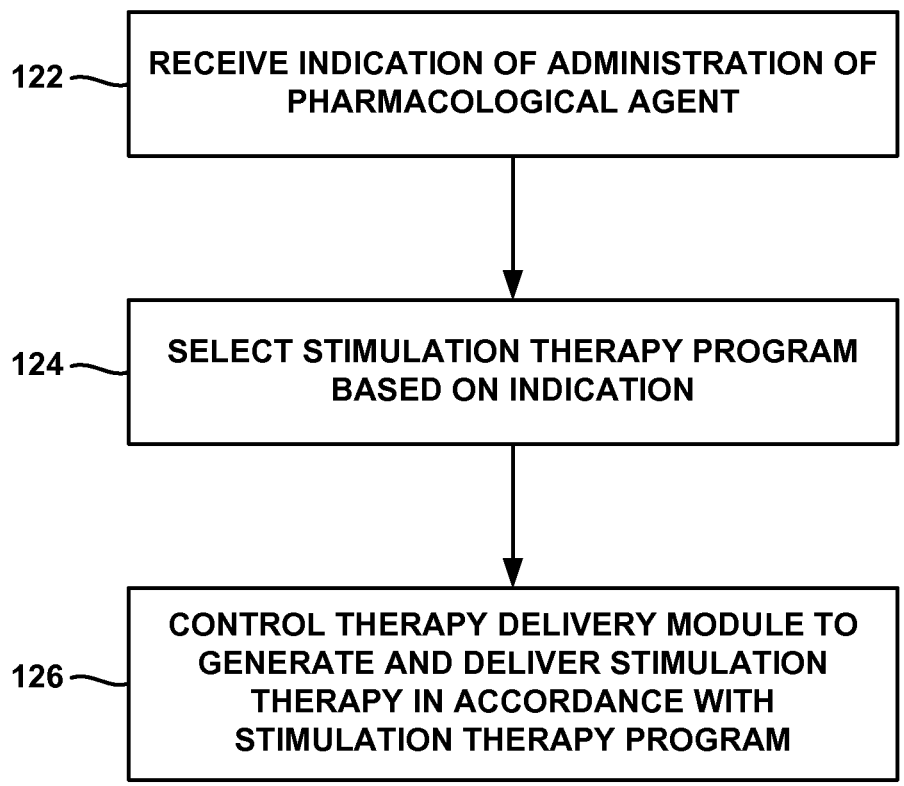
FIG. 9 is a flow diagram that illustrates an example technique according to which an IMD delivers stimulation therapy to a patient.

FIG. 9 is a flow diagram that illustrates an example of a technique which control module 50 of IMD 16 may implement to deliver stimulation therapy to patient 14. Initially, control module 50 may receive an indication of administration of a pharmacological agent to patient 14 in a manner that is configured to desensitize a C-afferent nerve fiber(s) of patient 14 (122). As described above, in some examples, the pharmacological agent is administered by a clinician, while in other examples, the pharmacological agent is administered via implantable drug delivery device 42.

In examples in which a clinician administers the pharmacological agent, one or both programmers 24, 46 may include a user interface element, e.g., a user interface screen, a button, or the like, that allows a user, such as the clinician or patient 14, to input an indication that the pharmacological agent has been administered to patient 14. In some implementations, control module 90, 102 of the programmer 24, 46 may present a user interface element or screen via the respective user interface 94, 104 that allows the user to input the indication.

One or both control modules 90, 102 may receive the indication from the user via the respective user interfaces 94, 104 and may control the respective telemetry module 96, 108 to transmit the indication to control module 50 of IMD 16 via telemetry module 58 of IMD 16. Control module 50 then receives the indication (122).

In examples in which implantable drug delivery device 42 administers the pharmacological agent, device 42 may generate and transmit the indication to IMD 16, programmer 24, or programmer 46 upon administering the agent to patient 14. For example, control module 70 of implantable drug delivery device 42 may control fluid delivery pump 76 to deliver the pharmacological agent to patient 14 via catheter 44. In some examples, control module 70 may then control telemetry module 74 of implantable drug delivery device 42 to transmit the indication of the delivery of the pharmacological agent to control module 90 of programmer 24 directly via telemetry module 96. In other examples, control module 70 of device 42 may control telemetry module 74 of implantable drug delivery device 42 to transmit the indication of the delivery of the pharmacological agent to control module 102 of programmer 46 via telemetry module 108. Control module 102 of programmer 46 then may control telemetry module 108 to transmit the indication to control module 90 of programmer 24 via telemetry module 96. Regardless, once control module 90 of programmer 24 receives the indication that implantable drug delivery device 42 has administered the pharmacological agent to patient 14, control module 90 may cause telemetry module 96 to transmit the indication to control module 50 of IMD 16 automatically or under control of a user, such as a clinician or patient 14. Control module 50 receives the indication (122).

In other examples, control module 70 of implantable drug delivery device 42 may control fluid delivery pump 76 (FIG. 5) to deliver the pharmacological agent to patient 14 via catheter 44. In some examples, control module 70 may then control telemetry module 74 of implantable drug delivery device 42 to transmit the indication of the delivery of the pharmacological agent directly to control module 50 of IMD 16 via telemetry module 58. Control module 50 receives the indication (122).

Regardless of the manner by which control module 50 of IMD 16 receives the indication (122), control module 50 may select one of stimulation therapy programs 66 based on the received indication, e.g., in response to receiving the indication (124). In some examples, the indication may simply indicate that the pharmacological agent has been administered to patient 14, and control module 50 may execute instructions stored in memory 56 to determine which of stimulation therapy programs to select in response to receiving the indication. In other examples, the indication may indicate one or more specific stimulation therapy program or a group of stimulation therapy programs from which control module 50 is to select. Alternatively or additionally, the indication may include stimulation parameters that together define a stimulation therapy program, and control module 50 may select or implement a stimulation therapy program that includes the stimulation parameters received with the indication.

In some examples, control module 50 may select one of the stored stimulation therapy programs 66 from memory 56 (FIG. 4), where the stimulation program is selected to include stimulation parameters that define a higher stimulation intensity than control module 50 would otherwise select if the pharmacological agent had not been administered to patient 14. As described above, in some examples, desensitization of the C-afferent nerve fiber(s) by the pharmacological agent may facilitate use of a higher stimulation intensity by reducing discomfort or pain experienced by patient 14 due to the stimulation therapy.

In other examples, control module 50 may select one of stimulation therapy programs 66 that includes stimulation parameters that define a relatively lower stimulation intensity (e.g., within a range of stimulation intensities which IMD 16 would select when the pharmacological agent had not been administered to patient 14). As described above, in some examples, C-afferent fiber(s) that innervate bladder 12 may promote contraction of bladder 12, thus inhibiting an efficacy of the stimulation therapy when the C-afferent fiber(s) are activated. In some examples, desensitization of the C-afferent fiber(s) may therefore increase an efficacy of the stimulation therapy delivered by IMD 16. IMD 16 may then deliver the stimulation therapy to patient 14 in accordance with the selected one of stimulation therapy programs 66.

Once control module 50 has selected one of stimulation therapy programs 66 based on the received indication (124), control module 50 controls therapy delivery module 52 to generate and deliver electrical stimulation therapy via electrodes 29 to a target therapy site in patient 14 in accordance with the stimulation therapy program (126).

As described above, the stimulation therapy may activate a nerve fiber in the tissue site. The activated nerve fiber may be different than the desensitized C-afferent nerve fiber(s). In some examples, the nerve that comprises the desensitized C-afferent nerve fiber(s) also includes the nerve fiber that is activated by the stimulation therapy. In other examples, the nerve that includes the desensitized C-afferent nerve fiber(s) is different than the nerve that includes the nerve fiber that is activated by the stimulation therapy. The nerve fiber that is activated by the stimulation therapy may include an afferent nerve fiber, such as an A-Beta (Aβ) afferent nerve fiber or an A-Delta (Aδ) afferent nerve fiber, may include an efferent nerve fiber, or both. In some examples, the nerve fiber that is activated by the stimulation therapy is an afferent nerve fiber (i.e., includes substantially only afferent nerve fiber and substantially no efferent nerve fiber). In other examples, the nerve fiber that is activated by the stimulation therapy is an efferent nerve fiber (i.e., includes substantially only efferent nerve fiber and substantially no afferent nerve fiber).

Figure 10:
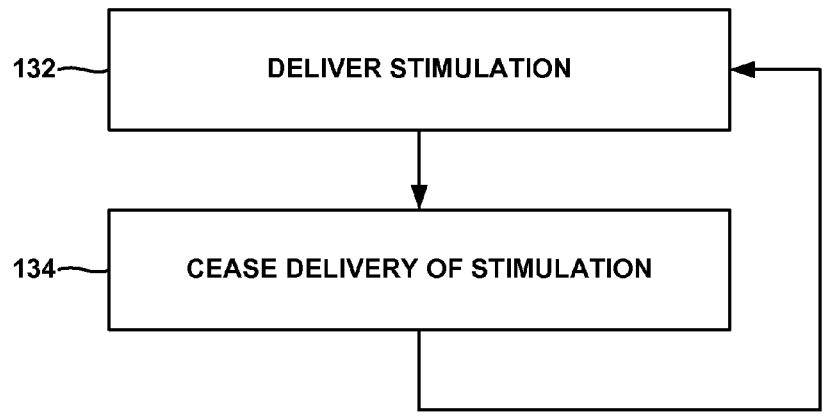
FIG. 10 is a flow diagram that illustrates an example technique for delivering stimulation therapy that includes a plurality of alternating first and second time periods to manage a bladder dysfunction.

As described above, in some examples, IMD 16 may deliver stimulation therapy that includes a plurality of interleaved first and second time periods, during which IMD 16 delivers stimulation therapy according to different stimulation parameters. FIG. 10 is a flow diagram that illustrates an example of a technique for delivering stimulation therapy that includes a plurality of alternating first and second time periods to manage bladder dysfunction. Under control of control module 50, therapy delivery module 52 of IMD 16 delivers stimulation therapy to patient 14 according to a therapy program (132). In some examples, control module 50 initiates the delivery of the first stimulation therapy by therapy delivery module 52 upon activation of chronic therapy delivery by the clinician via programmer 24. Therapy delivery module 52 delivers the stimulation therapy chronically, e.g., for an extended period of time, such as hours, days, weeks, or longer.

As described above, the stimulation therapy may include a first time period during which therapy delivery module 52 delivers stimulation to patient 14 according to a therapy program and a second time period during which therapy delivery module 52 does not deliver stimulation to patient 14, i.e., in which delivery of stimulation is ceased (134). The first and second time periods generally alternate, such that the second time period may begin immediately upon the ending of the first time period. Similarly, the stimulation therapy continues with another first time period immediately upon the ending of the second time period. In this way, the first and second time periods may alternate periodically to define the stimulation therapy delivered by therapy delivery module 52.

Each of the first and second time periods may include a predetermined duration, which may be stored in the respective stimulation therapy programs 66 in memory 56 of IMD 16. In some examples, the duration of each of the first time periods is greater than about 5 minutes, such as between about 5 minutes and about 20 minutes, or about 10 minutes. In some examples, the duration of each of the second time periods is greater than about 5 minutes, such as between about 5 minutes and about 30 minutes, or between about 10 minutes and about 20 minutes. In some implementations, the durations of the first time periods and the second time periods are the same, which in other implementations, the durations of the first time periods and the second time periods are different.

The time periods may be selected based on various factors. For example, as discussed above, stimulation during the first time period may generate a delayed physiological response from patient 14 that helps prevent the occurrence of an involuntary voiding event, whereby the physiological response is more pronounced during the second time period that follows the first time period. The physiological response may not be generated until the first stimulation therapy is delivered to patient 14 for at least a minimum duration of time (e.g., at least about 5 minutes, such as between about 5 minutes and about 30 minutes or about 10 minutes). Thus, the first time period may be selected to be the time period sufficient to generate the desired physiological response (e.g., a particular percentage of bladder contraction frequency or a particular bladder contraction frequency value) during the second time period.

Upon the ending of the first time period, therapy delivery module 52, under the control of control module 50, ceases delivering stimulation to patient 14 according to the therapy program, and in some cases, ceases delivery of all stimulation (134), for the duration of the second time period. Conversely, at the end of the second time period, therapy delivery module 52 initiates delivery of stimulation to patient 14 (132). Together, the first and second time periods define the stimulation therapy delivered to patient 14 by therapy delivery module 52.

During the first time periods, therapy delivery module 52 may deliver stimulation therapy that elicits either substantially no inhibitory physiological response related to voiding of patient 14 or first inhibitory physiological response related to voiding of patient 14. As described above, in some examples, the first and second inhibitory physiological responses related to voiding include a reduction in contraction frequency of bladder 12.

The stimulation therapy delivered to patient 14 by therapy delivery module 52 elicits a second physiological response related to voiding of patient 14 during the second time period which, for at least a portion of the second time period, is greater than the first physiological response of patient 14. For example, a contraction frequency of bladder 12 during at least a portion of the second time period may be lower than a contraction frequency of bladder 12 during the first time period. In this way, the stimulation therapy delivered by therapy delivery module 52 elicits a post-stimulation inhibitory effect that extends beyond the first time period, into the second time period. Because the second physiological response may not be observed during the first time period, the second physiological response may also be referred to as a delayed physiological response elicited by the delivery of the first stimulation therapy according to the therapy program during the first time period.

As described above, in some examples the stimulation parameters according to which therapy delivery module 52 delivers stimulation during the first time periods may define a stimulation intensity below a threshold intensity. In other examples, the stimulation parameters according to which therapy delivery module 52 delivers stimulation during the first time periods may define a stimulation intensity that is approximately equal to the threshold intensity or is above the threshold stimulation intensity. For example, as described above, the stimulation parameters may define a stimulation intensity that is between about 100% and about 300% of the threshold intensity.

Figure 11:
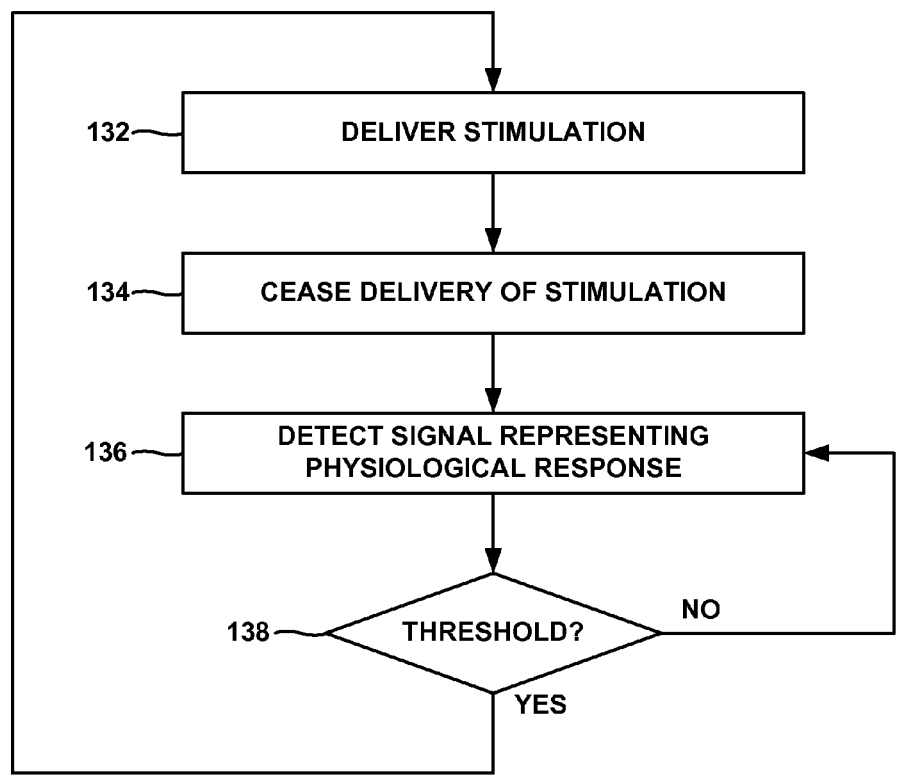
FIG. 11 is a flow diagram that illustrates an example technique for delivering stimulation therapy that includes a first time period during which an IMD delivers stimulation to the patient and a second time period during which the IMD does not deliver stimulation to the patient.

FIG. 11 is a flow diagram illustrating an example technique for delivering closed loop therapy including a first time period during which therapy delivery module 52 delivers stimulation to patient 14 and a second time period during which therapy delivery module 52 does not deliver stimulation to patient 14. In the example illustrated in FIG. 11, the duration of the second time period may be adjusted by control module 50 in response to an input received from sensor 22 or electrodes 19 and/or 21. In other examples, the duration of the second time period may be adjusted in response to another input, e.g., from a user such as patient 14 or a clinician or another sensing module of therapy system 10. In some examples, in addition to or as an alternative to adjusting the duration of the second time period, the duration of the first time period may be adjusted based on an input received by control module 50, e.g., from patient 14 or from a sensor.

Initially, control module 50 controls therapy delivery module 52 to deliver stimulation to patient 14 via electrodes 29, where the stimulation is defined by a therapy program (132). As described above, the stimulation therapy delivered during the first time period according to the therapy program may elicit substantially no inhibitory physiological response related to voiding in patient 14 during the first time period, or may elicit a first inhibitory physiological response related to voiding in patient 14 during the first time period. In some examples, the first inhibitory physiological response related to voiding includes a reduction in contraction frequency of bladder 12. In some examples, the duration of the first time period is greater than about 5 minutes, such as between about 5 minutes and about 20 minutes, or about 10 minutes.

In some examples, the stimulation parameters according to which therapy delivery module 52 delivers the stimulation therapy during the first time period define a stimulation intensity that is less than a threshold stimulation intensity, as described above. In other examples, the stimulation parameters define a stimulation intensity that is substantially equal to the threshold stimulation intensity, or is greater than the threshold stimulation intensity.

At the end of the first time period, control module 50 controls therapy delivery module 52 to cease delivering stimulation (134) and detects a signal indicative of a physiological response of patient 14 to the stimulation delivery according to the therapy program during the first time period (136). The signal may be, for example, generated by sensor 22 (FIG. 4), impedance module 54, or by another sensor. For example, in some examples, control module 50 monitors contraction of bladder 12. In some examples, control module 50 may monitor impedance of bladder 12 to detect contraction of bladder 12 based on signals received from impedance module 54, such as by comparing the determined impedance value to a threshold impedance value stored in memory 56 as bladder data 69. In some implementations, control module 50 monitors impedance of bladder 12 for a predetermined duration of time to detect contractions of bladder 12. In other examples, when the determined impedance value is less than the threshold impedance value stored in bladder data 69, control module 50 detects bladder contraction of sufficient intensity to warrant delivery of the stimulation therapy (132).

In other examples, control module 50 may monitor signals received from sensor 22 to detect contraction of bladder 12. As previously described, sensor 22 may comprise a pressure sensor for detecting changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy), or any combination thereof. For example, sensor 22 may be a pressure sensor for detecting changes in pressure of bladder 12, which control module 50 may correlate to contractions of bladder 12. Control module 50 may determine a pressure value based on signals received from sensor 22 and determine whether the signal is indicative of a contraction of bladder 12 based on the pressure value.

One type of bladder contraction detection algorithm indicates an occurrence of a bladder contraction upon sensing of a signal that exhibits a certain characteristic, which may be a time domain characteristic (e.g., a mean, median, peak or lowest signal amplitude within a particular time period) or a frequency domain characteristic (e.g., an energy level in one or more frequency bands or a ratio of energy levels in different frequency bands). For example, the bladder contraction detection algorithm may indicate the occurrence of a bladder contraction when the amplitude of the signal from sensor 22 meets a certain condition relative to a threshold (e.g., is greater than, equal to or less than the threshold). Another bladder contraction detection algorithm indicates the occurrence of a bladder contraction if a sensed signal substantially correlates to a signal template, e.g., in terms of frequency, amplitude and/or spectral energy characteristics. Control module 50 may use known techniques to correlate a sensed signal with a template in order to detect the bladder contraction or detect the bladder contraction based on the frequency domain characteristics of a sensed signal. Other bladder contraction techniques may be used.

In examples in which sensor 22 includes an EMG sensor, control module 50 may generate an EMG from the received signals generated by sensor 22 (e.g., which may sense the muscle activity with one or more sensor positioned near the target muscle) and compare the EMG to one or more templates stored as bladder data 69 to determine whether the EMG is indicative of a bladder contraction.

Regardless of the manner by which control module 50 monitors contraction of bladder 12, control module 50 may determine the contraction frequency of bladder 12 by determining a number of contractions of bladder 12 in the predetermined duration of time. Control module 50 then may compare the contraction frequency of bladder 12 to a threshold contraction frequency or a baseline contraction frequency (138). As described above, the baseline contraction frequency may be contraction frequency of bladder 12 at a time prior to delivery of stimulation therapy by therapy delivery module 52 (e.g., prior to initiation of the technique illustrated in FIG. 11) and when no efficacious effects of stimulation therapy are observed. A threshold contraction frequency may be a predetermined percentage of the baseline contraction frequency or a percentage of the baseline contraction frequency input by a user via programmer 24. As one example, the threshold frequency may be between approximately 75% and approximately 100% of the baseline contraction frequency. As another example, the threshold contraction frequency may instead be based on clinical data collected from a plurality of patients.

When control module 50 determines that the contraction frequency of bladder 12 is above the threshold value or within a predetermined amount of the baseline contraction frequency, control module 50 may cause therapy delivery module 52 to initiate delivery of stimulation to patient 14 (132). However, when control module 50 determined that the contraction frequency of bladder 12 is below the threshold value or within a predetermined amount of the baseline contraction frequency, control module 50 may continue to detect the signal representing the physiological response (136) until the bladder contraction frequency of interest is detected. Delivery of stimulation at a time period prior to the detection of the bladder contraction frequency that is above the threshold value or within a predetermined amount of the baseline contraction frequency may not provide a significant therapeutic advantage to patient 14, because the bladder contraction frequency may indicate that the therapeutic effects of the delivery of stimulation according to the therapy program during the immediately preceding first time period are still present. In this way, delivery of stimulation according to the technique shown in FIG. 11 may be efficient because it may limit the extent to which therapy that may not have a significant impact on patient 14 is delivered.

The steps of delivering of the first stimulation therapy and monitoring of the patient to detect contractions of bladder 12 are illustrated in FIG. 11 as occurring sequentially. In other examples, these steps may be performed simultaneously instead of sequentially. For example, control module 50 may detect a signal representing a physiological response (136) while controlling therapy delivery module 52 to delivery stimulation therapy (132) and after controlling therapy delivery module 52 to cease delivery of stimulation therapy (134).

While the foregoing description has primarily been directed to desensitizing C-afferent nerve fiber(s) and delivering electrical stimulation therapy to manage urgency or other bladder dysfunction, in some examples, the techniques described herein may be adapted for use for managing pelvic pain. For example, a pharmacological agent such as those described herein may be administered to a patient to desensitize a C-afferent fiber(s) prior to delivering electrical stimulation therapy to manage pelvic pain, or during delivery of stimulation therapy to manage pelvic pain. As described herein, the pharmacological agent may be delivered to desensitize a C-afferent fiber(s) in the nerve to which electrical stimulation therapy is delivered or in a nerve other than the nerve to which the electrical stimulation therapy is delivered.

Additionally or alternatively, although the foregoing description has primarily been directed to delivering a pharmacological agent to directly desensitize a C-afferent fiber(s), in other examples, a pharmacological agent may be delivered to other portions of the nervous system, such as the spinal cord, in combination with delivering stimulation therapy to manage bladder dysfunction or pelvic pain. For example, a neurokinin 1 (NK1) receptor antagonist, an opioid, or morphine could be administered to the spinal cord or central nervous systems in combination with delivering electrical stimulation therapy to manage bladder dysfunction or pelvic pain.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, fluid delivery devices, or other devices. The term "control module," "processor" or "processing circuitry" may generally refer to any of the foregoing logic circuitry, alone or in combination with other logic circuitry, or any other equivalents.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

If implemented in software, the techniques described in this disclosure may be stored on or transmitted over as one or more instructions or code on a computer-readable medium. Computer-readable media may include non-transitory computer data storage media, which may be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. The code may be executed by one or more processors, such as one or more DSPs, general purpose microprocessors, ASICs, FPGAs, or other equivalent integrated or discrete logic circuitry. Accordingly, the term "control module" or "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

EXAMPLES

Female Sprague-Dawley rats weighing approximately 200-300 grams (g) were anesthetized with urethane (in particular, two injections, approximately 4 min apart, total 1.2 g urethane/kilogram (kg) rat). The anesthetized rats were maintained with a hot-water-circulating heating pad during the studies.

To record bladder contractions, a polyethylene cannula (IntraMedic PE50 tubing, Stoelting Co., Wood Dale, Ill.), was placed into the bladder of each of the rats via the urethra and the urethra was ligated to ensure an isovolumetric bladder. The urethral cannula was connected with a T connector and linked with a low volume transducer (ADInstrument MLT0380/D, Colorado Springs, Colo.). The signal was amplified through a DC amplifier (ADInstrument, ML119, Colorado Springs, Colo.). The other end of the T connector was linked to a 20 cubic centimeters (cc) syringe with a perfusion pump.

To deliver electrical stimulation, a wire electrode was placed under the L6 spinal nerves of each of the rats bilaterally. The dorsal skin around sacral and thoracic surface was shaved and a dorsal midline incision was made from approximately spinal nerve L3 to S2. A combination of sharp and blunt dissection was used to expose the left L6/S1 posterior interarticular process. The S1 transverse process was visualized and removed, and the L6 nerves were located caudal and medial to the sacroiliac junction and were then exposed distal to their emergence from the intervertebral foramina. Two bared portions of a teflon-coated, 40-gauge, stainless steel wire (Cooner Wire Co., Chatsworth, Calif.) were placed bilaterally under each of the L6 nerve. A silicone adhesive (Kwik-Cast, World Precision Instruments, Inc, Sarasota, Fla.) was applied to cover the wire around the nerve. The muscle and incision were closed with silk suture. The wire electrode and a needle electrode under the skin of the tail served as the stimulating cathode and the indifferent anode, respectively.

Biphasic pulses having a pulse width of about 0.1 ms and different intensities were used to stimulate the spinal nerve at frequencies ranging from 0.01 Hz to 100 Hz. A Grass S88 stimulator (Grass Technologies, West Warwick, R.I.) with an SIU5 stimulus isolator (Grass Technologies, West Warwick, R.I.) was used to generate stimulus pulses. Electrical stimulation of spinal nerves with pulses of sufficient intensity evoked hind-toe twitches and pelvic floor muscle contractions. In each rat, the motor threshold, defined by the lowest intensity to evoke any of those muscle contractions was tested. The rats with motor threshold over 0.4 mA were excluded from the study. The intensities of stimulation were given either at 0.6 mA or threshold intensity, which was adjusted until the muscle contraction was just discernible in each animal.

Thirty-two rats were chronically treated with capsaicin or vehicle (e.g., solution without capsaicin added). Capsaicin (Sigma-Aldrich, St. Louis, Mo.) was administered to the rats in a vehicle solution containing approximately 20 milligrams (mg)/milliliters (mL) capsaicin in a mixture of approximately 10% ethanol, approximately 10% Tween 80 and approximately 80% physiological saline. For each of the rats, capsaicin (125 mg/kg) was given subcutaneously in the hindlimb in divided doses on 2 consecutive days: on the first day, a first dose of 25 mg/kg was administered, and, twelve hours later, a second dose of 50 mg/kg was administered, and on the second day, a third dose of 50 mg/kg was administered. Injections were performed under isoflurane anesthesia. Control rats received a corresponding volume of vehicles. Experiments on the effect of neurostimulation on rhythmic bladder contraction were conducted approximately 4 days after injection of the third dose was administered. To evaluate the effectiveness of capsaicin pretreatment, an eye wipe test was performed on each unanesthetized animal just before the experiment. A drop of approximately 100 microgram per milliliter (μg/mL) capsaicin solution was instilled into an eye of the animal and the number of defensive wiping movements was counted. After the eye wipe test, the eye was irrigated with physiological saline and the animals were anesthetized to conduct neurostimulation studies.

All data were expressed as mean±standard error measurement. Results were analyzed with Student's two sample t-test or analysis of variance (ANOVA) with repeated measures by Prism 4 (GraphPad Software, Inc., San Diego, Calif.). A value of p<0.05 was considered statistically significant. P value is the probability of obtaining a test statistic at least as extreme as the one that was actually observed, assuming that the null hypothesis is true. The lower the p-value, the less likely the result is false if the null hypothesis is true, and consequently the more "significant" the result is, in the sense of statistical significance. A p value of 0.05 corresponds to a 5% chance of rejecting the null hypothesis when it is true.

Following approximately 3-4 hours of the first capsaicin injection, the capsaicin treated rats showed signs of pain behaviors, e.g., involuntary twitching, hyperactivity and/or immobility. Thereafter no aversive behaviors were observed in capsaicin-treated rats. On the day before the neurostimulation studies (discussed before), the effectiveness of capsaicin pretreatment was demonstrated by showing no reaction in the eye wipe test in capsaicin treated rats (16 rats) to a drop of 100 μg/mL capsaicin solution (vehicle controls: 11.38±1.06 wipings in 20 seconds, 16 rats).

Four days after capsaicin or vehicle treatment, the rats were subjected to neurostimulation, e.g., electrical stimulation, studies to determine the effect of neuromodulation on the bladder rhythmic contraction. For the study of the effect of neuromodulation on the bladder rhythmic contraction, the saline was infused into the bladder at a rate of approximately 50 μL per minute to induce micturition reflex (defined in this example as bladder contraction with an intensity greater than about 10 millimeters of mercury (mmHg)). The infusion rate was then lowered to approximately 10 μL per minute until 3-5 rhythmic bladder contractions per 5 minutes were established; the infusion of the saline was then terminated. The nerve stimulation was delivered beginning approximately 15 minutes after termination of the infusion of saline. The stimulation was delivered for approximately 10 minutes and bladder rhythmic contractions were recorded for 20 minutes post nerve stimulation. Two parameters of the bladder rhythmic contraction were evaluated: frequency and amplitude. The mean controls were calculated by the average of readouts during the last approximately 5 minute interval of the approximately 15 minute period after infusion was terminated and before stimulation was delivered. The effects of nerve stimulation were calculated by the mean response (e.g., bladder contraction frequency and bladder contraction amplitude) in every approximately 5 minute period.

Prior to delivery of neurostimulation, it was found that the mean frequency and amplitude (mean controls) of bladder contractions did not differ between capsaicin-treated rats and vehicle-treated rats. Capsaicin-treated rats (8 rats) averaged approximately 3.19±0.20 contractions per 5 minutes with an average amplitude of approximately 19.24±1.89 mmHg, while vehicle-treated rats (8 rats) averaged approximately 2.81±0.38 contractions per 5 minute with an average amplitude of 20.63±2.73 mmHg.

Figure 12A:
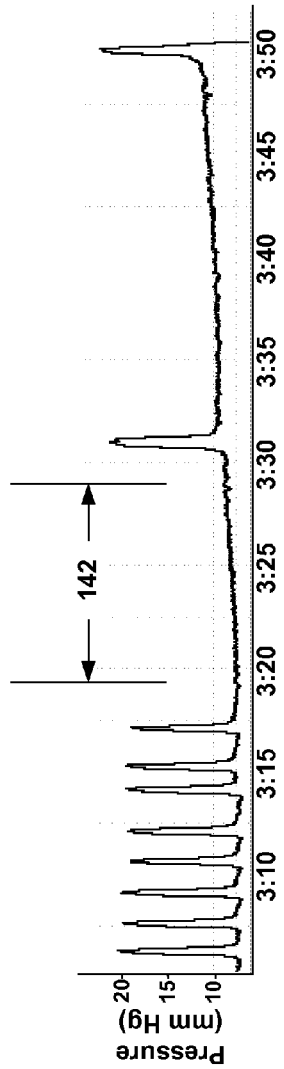
FIGS. 12A and 12B are diagrams that illustrate amplitude of bladder contractions versus time.
Figure 12B:
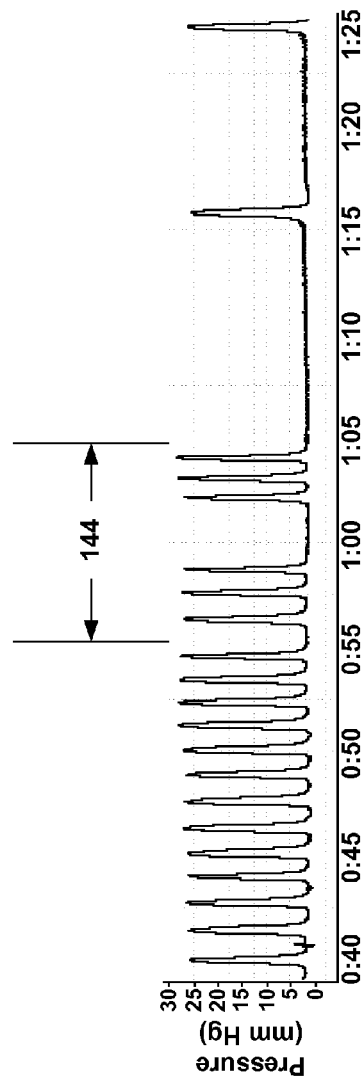

FIGS. 12A and 12B are diagrams that illustrate amplitude of bladder contractions versus time in rats with capsaicin (125 mg/kg, subcutaneous introduction) pretreatment 4 days before the bladder rhythmic contraction study. FIG. 12A shows that the rhythmic bladder contractions were substantially completely inhibited by spinal nerve stimulation delivered during time period 142 at an intensity of approximately 0.6 mA, and a frequency of 0.5 Hz. This inhibition persisted for more than 20 minutes even after the stimulation was terminated. FIG. 12B shows that spinal nerve stimulation delivered during time period 144 at the threshold intensity (about 0.01 mA) and a frequency of about 10 Hz attenuated bladder contractions, particularly after termination of electrical stimulation.

Figure 13A:
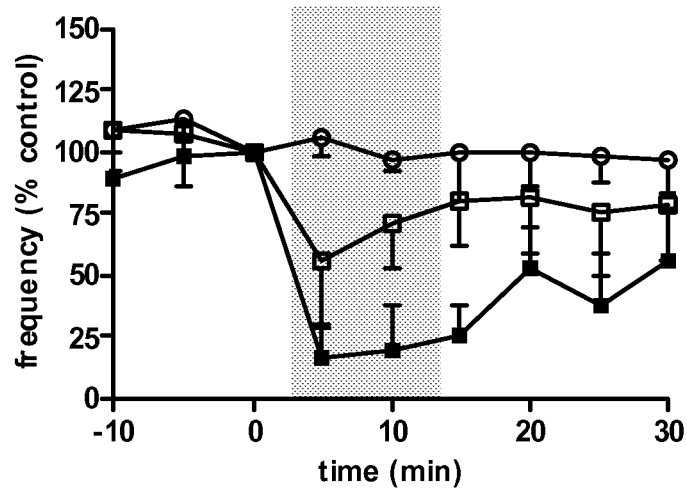
FIGS. 13A and 13B are line diagrams that summarize the effect of spinal nerve stimulation.
Figure 13B:
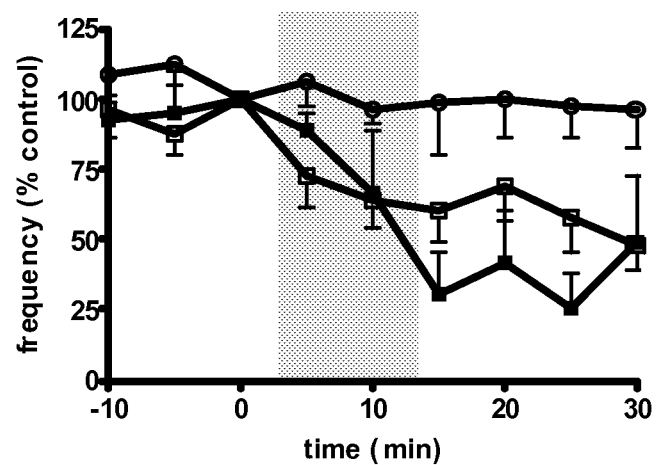

FIGS. 13A and 13B are line diagrams that summarize the effect of spinal nerve stimulation delivered at an intensity of approximately 0.6 mA (FIG. 13A) and at the threshold intensity (FIG. 13B). For each stimulation intensity, results are shown for control animals (not subjected to neurostimulation), animals pretreated with capsaicin (approximately 125 mg/kg s.c.), and animals pretreated with vehicle. The results of the above-described test indicated that, in capsaicin pretreated rats, relatively high intensity stimulation (approximately 0.6 mA, FIGS. 12A and 13A) produced a stronger inhibition on frequency of the bladder rhythmic contraction than in vehicle pretreated rats (18±14% of control (open circles in FIG. 13A) for six capsaicin pretreated rats (solid squares in FIG. 13A, versus 63±17% of control in seven vehicle pretreated rats (open squares in FIG. 13A); p<0.05, two-way ANOVA). Stimulation at threshold intensity (approximately 0.01 mA, FIG. 13B) showed a trend of inhibitory effects on bladder rhythmic contraction, but it is believed that such inhibition is not statistically significant. In FIGS. 13A and 13B, solid squares represent data collected for capsaicin pretreated rats, open squares represent data collected for vehicle pretreated rats, and open circles represent data collected for control rats (e.g., rats that did not receive capsaicin treatment or electrical stimulation therapy).

What is claimed is:

1. A method comprising:
    administering a pharmacological agent to a patient in a dosage sufficient to desensitize a C-afferent nerve fiber of the patient; and
    delivering electrical stimulation to activate a nerve fiber proximate to the C-afferent nerve fiber via an electrode electrically coupled to an implantable medical device, wherein the nerve fiber is different than the C-afferent nerve fiber, wherein the stimulation of the nerve fiber elicits an inhibitory physiological response related to voiding in the patient, and wherein the stimulation substantially does not activate the C-afferent nerve fiber after desensitization of the nerve fiber via the administration of the pharmacological agent.

2. The method of claim 1, wherein the nerve fiber comprises at least one of an A-delta (Aδ) nerve fiber or an A-beta (Aβ) nerve fiber.

3. The method of claim 1, wherein the nerve fiber is an efferent nerve fiber.

4. The method of claim 1, wherein the nerve fiber forms a portion of at least one of a spinal nerve, a sacral nerve, a pelvic nerve, a pudendal nerve, dorsal genital nerve, a tibial nerve, an inferior rectal nerve, or a perineal nerve.

5. The method of claim 1, wherein the inhibitory physiological response comprises a reduction of a frequency of bladder contractions of the patient.

6. The method of claim 1, wherein delivering stimulation to the nerve fiber proximate to the C-afferent nerve fiber via the electrode electrically coupled to the implantable medical device comprises delivering stimulation to the nerve fiber proximate to the C-afferent nerve fiber via the electrode electrically coupled to the implantable medical device at a pulse frequency of less than about 60 Hz.

7. The method of claim 1, wherein delivering stimulation to the nerve fiber proximate to the C-afferent nerve fiber via the electrode electrically coupled to the implantable medical device comprises delivering stimulation to the nerve fiber proximate to the C-afferent nerve fiber via the electrode electrically coupled to the implantable medical device at a pulse frequency of between about 0.1 Hz and about 20 Hz.

8. The method of claim 1, wherein delivering stimulation to the nerve fiber proximate to the C-afferent nerve fiber via the electrode electrically coupled to the implantable medical device comprises delivering stimulation to the nerve fiber proximate to the C-afferent nerve fiber via the electrode electrically coupled to the implantable medical device at a stimulation intensity of between about one-half of a threshold stimulation intensity and about three times the threshold stimulation intensity.

9. The method of claim 1, wherein delivering stimulation to the nerve fiber proximate to the C-afferent nerve fiber via the electrode electrically coupled to the implantable medical device comprises:
  delivering stimulation at a first stimulation intensity during a first time period, wherein the stimulation elicits a first inhibitory physiological response related to voiding in the patient during the first time period, and wherein the first time period is at least about 5 minutes;
  delivering stimulation at a second stimulation intensity during a second time period immediately following the first time period, wherein the second stimulation intensity is less than the first stimulation intensity, wherein the stimulation elicits a second inhibitory physiological response related to voiding in the patient during the second time period, wherein the second inhibitory physiological response is greater than the first inhibitory physiological response, and wherein the second time period is at least about 5 minutes; and
  delivering stimulation at the first stimulation intensity during a third time period, wherein the third time period immediately follows the second time period.

10. The method of claim 1, wherein administering the pharmacological agent to the patient comprises administering at least one of a sodium channel blocker, a calcium channel blocker, botulinum toxin, or capsaicin to the patient.

11. The method of claim 1, wherein administering the pharmacological agent to the patient comprises administering the pharmacological agent to the patient via intravesical injection in a bladder of the patient.

12. The method of claim 1, wherein administering the pharmacological agent to the patient comprises administering the pharmacological agent to the patient via a catheter fluidically coupled to an implantable drug delivery device.

13. A method comprising:
  receiving via a control module of an implantable medical device an indication that a pharmacological agent has been administered in a dosage sufficient to desensitize a C-afferent nerve fiber to a patient in which the implantable medical device is implanted;
  selecting via the control module an electrical stimulation therapy program based on the received indication; and
  controlling via the control module a therapy delivery module to generate and deliver electrical stimulation therapy in accordance with the electrical stimulation therapy program to activate a nerve fiber proximate to the C-afferent nerve fiber, wherein the nerve fiber is different than the C-afferent nerve fiber, wherein the electrical stimulation therapy elicits an inhibitory physiological response related to voiding in the patient, and wherein the electrical stimulation therapy substantially does not activate the C-afferent nerve fiber after desensitization of the nerve fiber via the administration of the pharmacological agent.

14. The method of claim 13, wherein the nerve fiber comprises at least one of an A-delta (Aδ) nerve fiber or an A-beta (Aβ) nerve fiber.

15. The method of claim 13, wherein the nerve fiber comprises an efferent nerve fiber.

16. The method of claim 13, wherein the nerve fiber forms a portion of at least one of a spinal nerve, a sacral nerve, a pelvic nerve, a pudendal nerve, dorsal genital nerve, a tibial nerve, an inferior rectal nerve, or a perineal nerve.

17. The method of claim 13, wherein the inhibitory physiological response comprises a reduction of a frequency of bladder contractions of the patient.

18. The method of claim 13, wherein the electrical stimulation therapy program defines a pulse frequency of the electrical stimulation therapy, and wherein the pulse frequency is less than about 60 Hz.

19. The method of claim 13, wherein the electrical stimulation therapy program defines a stimulation intensity, and wherein the stimulation intensity is between about one-half of a threshold stimulation intensity and about three times the threshold stimulation intensity.

20. The method of claim 13, wherein controlling via the control module the therapy delivery module to generate and deliver electrical stimulation therapy in accordance with the electrical stimulation therapy program comprises controlling via the control module the therapy delivery module to generate and deliver stimulation at a first stimulation intensity for a first time period, to deliver stimulation at a second stimulation intensity for a second time period immediately following the first time period, and to deliver stimulation at the first stimulation intensity for a third time period immediately following the second time period, wherein the second stimulation intensity is less than the first stimulation intensity, wherein each of the first time period, the second time period, and the third time period comprises at least five minutes, wherein the stimulation elicits a first inhibitory physiological response related to voiding in the patient during the first time period and elicits a second inhibitory physiological response related to voiding in the patient during the second time period, and wherein the second inhibitory physiological response is greater than the first inhibitory physiological response.

21. A computer-readable medium comprising instructions that cause a processor to:
  receive via an implantable medical device an indication that a pharmacological agent has been administered in a dosage sufficient to desensitize a C-afferent nerve fiber to a patient in which the implantable medical device is implanted;
  select an electrical stimulation therapy program based on the received indication; and
  control a therapy delivery module to generate and deliver electrical stimulation therapy in accordance with the electrical stimulation therapy program to activate a nerve fiber proximate to the C-afferent nerve fiber, wherein the nerve fiber is different than the C-afferent nerve fiber, wherein the electrical stimulation therapy elicits an inhibitory physiological response related to voiding in the patient, and wherein the electrical stimulation therapy substantially does not activate the C-afferent nerve fiber after desensitization of the nerve fiber via the administration of the pharmacological agent.

22. The computer-readable medium of claim 21, wherein the nerve fiber forms a portion of at least one of a spinal nerve, a sacral nerve, a pelvic nerve, a pudendal nerve, dorsal genital nerve, a tibial nerve, an inferior rectal nerve, or a perineal nerve.

23. The computer-readable medium of claim 21, wherein the inhibitory physiological response comprises a reduction of a frequency of bladder contractions of the patient.

24. The computer-readable medium of claim 21, wherein the electrical stimulation therapy program defines a pulse frequency of the electrical stimulation therapy, and wherein the pulse frequency is less than about 60 Hz.

25. A system comprising:
means for administering a pharmacological agent to a patient in a dose sufficient to desensitize a C-afferent nerve fiber; and
means for delivering electrical stimulation to activate a nerve fiber proximate to the C-afferent nerve fiber via an electrode electrically coupled to the means for delivering stimulation, wherein the nerve fiber is different than the C-afferent nerve fiber, wherein the stimulation of the nerve fiber elicits an inhibitory physiological response related to voiding in the patient, and wherein the stimulation substantially does not activate the C-afferent nerve fiber after desensitization of the nerve fiber via the administration of the pharmacological agent.

26. The system of claim 25, wherein the nerve fiber is an afferent nerve fiber.

27. The system of claim 25, wherein the nerve fiber is an efferent nerve fiber.

28. The system of claim 25, wherein inhibitory physiological response comprises a reduction of a frequency of bladder contractions of the patient.

29. The system of claim 25, wherein the pharmacological agent comprises at least one of a sodium channel blocker, a calcium channel blocker, botulinum toxin, or capsaicin.

30. A system comprising:
means for receiving an indication that a pharmacological agent has been administered to a patient in a dosage sufficient to desensitize a C-afferent nerve fiber in the patient;
means for selecting an electrical stimulation therapy program based on the received indication; and
means for generating and delivering electrical stimulation therapy in accordance with the electrical stimulation therapy program, wherein the electrical stimulation therapy program is configured to activate a nerve fiber proximate to the C-afferent nerve fiber, wherein the nerve fiber is different than the C-afferent nerve fiber, wherein the electrical stimulation therapy elicits an inhibitory physiological response related to voiding in the patient, and wherein the electrical stimulation therapy substantially does not activate the C-afferent nerve fiber.

31. The system of claim 30, wherein the nerve fiber is an afferent nerve fiber.

32. The system of claim 30, wherein the nerve fiber is an efferent nerve fiber.

33. The system of claim 30, wherein the inhibitory physiological response comprises a reduction of a frequency of bladder contractions of the patient.

34. The system of claim 30, wherein the pharmacological agent comprises at least one of a sodium channel blocker, a calcium channel blocker, botulinum toxin, or capsaicin.

* * * * *